US012724500B2

(12) United States Patent
Al-Hawas et al.

(10) Patent No.: US 12,724,500 B2
(45) Date of Patent: Sep. 1, 2026

(54) SMART STYLUS THERAPEUTIC SYSTEM AND METHOD OF USE

(71) Applicant: Imam Abdulrahman Bin Faisal University, Dammam (SA)

(72) Inventors: Razan Osama Al-Hawas, Dammam (SA); Hala El-Wakeel, Dammam (SA); Noran Kattan, Dammam (SA); Lama Alshehri, Dammam (SA); Lojain Alamri, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 19/339,853

(22) Filed: Sep. 25, 2025

(65) Prior Publication Data

US 2026/0023443 A1 Jan. 22, 2026

Related U.S. Application Data

(62) Division of application No. 18/598,029, filed on Mar. 7, 2024, now Pat. No. 12,468,405.

(51) Int. Cl.
*G06F 3/0354* (2013.01)
*G06F 3/041* (2006.01)
(Continued)

(52) U.S. Cl.
CPC ........ *G06F 3/03545* (2013.01); *G06F 3/0414* (2013.01); *G06F 3/04162* (2019.05);
(Continued)

(58) Field of Classification Search
None
See application file for complete search history.

(56) References Cited

U.S. PATENT DOCUMENTS 4,596,335 A 6/1986 Hull
5,214,428 A * 5/1993 Allen .................... G06V 10/17
250/221

(Continued)

FOREIGN PATENT DOCUMENTS

CN 2230236 Y 7/1996

OTHER PUBLICATIONS

New 3DS Xl/L1 Retractable Metal Stylus Pen ; https://xmods.co.za/nintendo-portable/738-new-3ds-xiii-retractable-metal-stylus-pen.html ; 4 Pages.

(Continued)

*Primary Examiner* — Parul H Gupta
(74) *Attorney, Agent, or Firm* — Oblon, McClelland, Maier & Neustadt, L.L.P.

(57) ABSTRACT

A smart stylus for use in hand therapy includes an elongate body having a stylus end, a central body, a C-shaped handle, and a handle end cap. The stylus end is connected to a first end of the central body and a second end of the central body is connected to a first end of the C-shaped handle. The central body is configured to taper in width and depth from the second end of the central body to the first end of the central body and the handle end cap is connected to a second end of the C-shaped handle. The length of the central body may be adjusted by sliding mechanisms. A pressure sensor measures the amount of force of the stylus tip on a therapeutic tablet. The therapeutic tablet presents therapy exercises and communicates therapy results to a physical therapist of the patient.

10 Claims, 17 Drawing Sheets

(51) Int. Cl.
*G06F 3/044* (2006.01)
*G16H 20/30* (2018.01)
*G16H 40/67* (2018.01)

(52) U.S. Cl.
CPC .......... *G06F 3/0441* (2019.05); *G06F 3/0442* (2019.05); *G16H 20/30* (2018.01); *G16H 40/67* (2018.01)

(56) References Cited

U.S. PATENT DOCUMENTS

| | | | | |
|---|---|---|---|---|
| 2007/0225125 | A1* | 9/2007 | Basyuk | A63B 23/16 482/44 |
| 2009/0251442 | A1 | 10/2009 | Nakata | |
| 2010/0324506 | A1* | 12/2010 | Pellegrino | A61B 18/1492 604/528 |
| 2012/0019488 | A1 | 1/2012 | McCarthy | |
| 2014/0035884 | A1* | 2/2014 | Oh | G06F 3/03545 345/179 |
| 2014/0163664 | A1* | 6/2014 | Goldsmith | A61B 17/0057 604/93.01 |
| 2016/0278791 | A1* | 9/2016 | Pellegrino | A61B 17/1642 |
| 2017/0056710 | A1* | 3/2017 | McCrea | A63B 21/154 |
| 2018/0133540 | A1* | 5/2018 | McCrea | A63B 21/4035 |
| 2019/0125376 | A1* | 5/2019 | Batchelor | A61B 17/285 |
| 2019/0126442 | A1* | 5/2019 | Batchelor | A61B 18/1445 |
| 2019/0182579 | A1* | 6/2019 | Kulkarni | H04R 1/105 |
| 2020/0246046 | A1* | 8/2020 | Gammie | A61B 17/3478 |
| 2021/0333875 | A1* | 10/2021 | Horii | G06T 7/74 |
| 2022/0249126 | A1* | 8/2022 | Gammie | A61B 17/3478 |
| 2025/0114659 | A1* | 4/2025 | Adkins | A63B 21/4035 |

OTHER PUBLICATIONS

Baseus BS-PS007 Smooth Writing Wireless Stylus Charging Case ; https://executiveample.com/baseus-bs-ps007-smooth-writing-wireless-stylus-charging-case/ ; 2 Pages.

* cited by examiner

Base Station
Mobile Network Service
Central Processors
Server
Database
Access Point
Satellite
Mobile Device Terminals
Internet
Fixed Terminals
Provisioning Tool
Secure Gateway
Cloud Controller
Cloud
Data Storage
Data Center

SMART STYLUS THERAPEUTIC SYSTEM AND METHOD OF USE

CROSS-REFERENCE TO RELATED APPLICATIONS

The present application is a Divisional of U.S. application Ser. No. 18/598,029, now allowed, having a filing date of Mar. 7, 2024.

BACKGROUND

Technical Field

The present disclosure is directed towards physical rehabilitation techniques, and more particularly, directed towards a smart stylus, a system incorporating the smart stylus, and method for hand therapy in stroke patients.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cases of strokes and subsequent paralysis are currently on the rise. In general, stroke is a medical condition including two major types, namely, ischemic stroke and hemorrhagic stroke. Ischemic stroke occurs when blood supply to a part of human brain is blocked or reduced. This prevents brain tissue from getting oxygen and nutrients resulting in death of brain cells within minutes. Hemorrhagic stroke occurs when a blood vessel in the brain ruptures or bursts, subsequently bleeding in the brain. A major complication of stroke is loss of muscle movement or paralysis. Paralysis is uncertain and depends on the type and intensity of stroke, adversely affecting one or more muscle in human body.

Traditionally there are several solutions to treat complications associated with stroke such as paralysis. In accordance with general consensus, the most effective way to treat stroke paralysis is to activate neuroplasticity. Neuroplasticity refers to a mechanism that the brain uses to heal by reorganizing nerve cells and forming new neural pathways. These new neural pathways allow healthy, undamaged portions of the brain to take over control from areas that were affected by the stroke. Therefore, by engaging neuroplasticity, the brain may grow new neural pathways to the paralysed muscles to help recover from paralysis. Neuroplasticity may be activated through high repetition of rehab exercises. This high repetition results in reinforced, new neural pathways. Subsequently, strengthening the newly formed neural pathways may result in stronger and more efficient connection between the brain and affected muscles. Rehab exercises include, but are not limited to, passive exercises, mental practice, electrical stimulation, acupuncture, and mirror therapy. Passive exercise refers to moving the paralysed muscles on behalf of a stroke patient by supplemental apparatuses and systems. Similarly, in electrical stimulation, supplemental apparatuses are used to stimulate the paralysed muscles using mild electrical stimulus. However, the aforementioned techniques have limitations in helping the stroke patient recover fully. Different age groups of patients respond differently to the above stated rehab exercises. With continuous increment of young stroke patients, some of the traditional methods are rendered useless due to their orthodox approach and dated protocols, which do not resonate with the younger generation of stroke patients. Hence, there arises a need for a modern and advanced method, system and apparatus to provide the necessary support to a stroke patient, including all age groups.

U.S. Pat. No. 4,596,335A describes a marking implement holder. The marking implement holder includes a guide arm and a support arm. The guide arm has a free end adapted to engage a marking surface and act as a guide when the holder is grasped and moved along the marking surface. The support arm extends from the guide arm and is spaced from the free end thereof. However, the marking implement holder is not adapted for therapy or for use with a tablet, nor does it have adjustable length or spaces for weights.

US20120019488A1 describes a stylus for use with a system having a touchscreen display coupled to a processor. The touchscreen display is configured to determine positional information of an object positioned within a display area of the touchscreen display. Further, the stylus includes a tip portion and housing, and is configured to transmit pressure and orientation information of the housing to the processor. However, the stylus is not adapted for therapy nor does have adjustable length or spaces for weights. Further, the tablet associated with the aforementioned publication is not programmed with therapy lessons to aid in rehabilitation.

CN2230236Y describes a utility model that relates to a corrector for exercising the finger shape of a pencil holder for training directional holding, which is composed of a holding body, wherein a positioning hole for the pencil holder is arranged on the holding body. One side of the holding body is a pencil-holding curved surface which emulates a forefinger and the other side is a pencil-holding curved surface which emulates a thumb. The lower part of the front end of the holding body is provided with a convex middle finger holding point. The corrector is sheathed on the proper position of a hard pencil and is naturally held in a space formed by the thumb, the forefinger and the middle finger and three fingers to directly touch a pencil rod, therefore, the utility model has the advantages of natural and comfortable pencil-holding finger shape, writing flexibility, high speed, small force, and unbroken nib and is beneficial for children who first learn writing to master correct pencil-holding posture. However, there is no mention that the device is adapted for therapy nor does it have adjustable length, a curved shape, communications circuitry, a pressure sensor, spaces for weights. Further, there is no communication with a tablet programmed with therapy games or lessons.

US20090251442A1 describes an electronic stylus pen with weight adjusting mechanism. The electronic stylus pen includes a pen body, a stepped portion arranged in the central portion of the pen body, a pen tip arranged at a tip end of the pen body, and a small-diameter portion arranged in an area between the stepped portion and the pen tip of the pen body. The diameter of the small-diameter portion is smaller than that of the pen body. Weight adjusting members are mounted at arbitrary positions of the small-diameter portion. However, there is no mention that the device is adapted for therapy nor does it have adjustable length, a curved shape, communications circuitry, a pressure sensor, spaces for weights or the curved configuration of the lessons smart pen of the present disclosure. Further, there is no communication with a tablet programmed with therapy games or lessons.

Each of the aforementioned prior arts suffer from one or more drawbacks hindering their adoption. Therefore, a need arises for better and more advanced techniques for the rehabilitation of paralyzed muscles. Accordingly, it is one object of the present disclosure to provide a smart stylus, and a smart stylus therapeutic system including the smart stylus and a therapeutic tablet for rehabilitation of paralysed hand muscles due to stroke.

SUMMARY

In an exemplary embodiment, a smart stylus for use in hand therapy is described. The smart stylus includes an elongate body having a stylus end, a central body, a C-shaped handle, and a handle end cap. The stylus end is connected to a first end of the central body, and a second end of the central body is connected to a first end of the C-shaped handle. The central body is configured to taper in width and depth from the second end of the central body to the first end of the central body and the handle end cap is connected to a second end of the C-shaped handle. Furthermore, the smart stylus includes a first sliding mechanism located between the central body and the first end of the C-shaped handle. Moreover, the smart stylus includes a second sliding mechanism located between the second end of the C-shaped handle and the handle end cap, and a length of the elongate body depends on an adjustment of the first sliding mechanism and the second sliding mechanism.

In another exemplary embodiment, a smart stylus therapeutic system for use in hand therapy is described. The smart stylus therapeutic system includes an elongate body having a stylus end, a central body, a C-shaped handle, and a handle end cap. The stylus end is connected to a first end of the central body, a second end of the central body is connected to a first end of the C-shaped handle, and the handle end cap is connected to a second end of the C-shaped handle. The smart stylus therapeutic system further includes a rechargeable battery located within the handle end cap, a microcontroller located within the central body, and operatively connected to the rechargeable battery, and a near field communications unit located within the central body and operatively connected with the microcontroller. Further, the smart stylus therapeutic system includes a therapeutic tablet including a touch screen. The therapeutic tablet includes a memory having program instructions including a hand therapy treatment plan and one or more processors configured to execute the program instructions to receive near field communications from the near field communications unit and display the hand therapy treatment plan and hand therapy exercises upon the touch screen. The hand therapy exercises are configured to direct a patient to write upon the touch screen with the stylus end while gripping the C-shaped handle. The hand therapy exercise may include, but not limited to, tracing exercises, therapeutic objectives, or a combination thereof. Moreover, the smart stylus therapeutic system includes a case configured to hold the elongate body and the therapeutic tablet, and a charging port located on the case and configured to mate with the handle end cap. In addition, the smart stylus therapeutic system includes a rechargeable battery located with the central body and an electromagnetic coil located within the handle end cap and connected to the rechargeable battery. The electromagnetic coil is configured to generate a charging current when the handle end cap is placed adjacent to the charging port.

In yet another exemplary embodiment, a method of using the smart stylus in hand therapy is described. The method includes forming an elongate body having a stylus end, a central body, a C-shaped handle, and a handle end cap. The stylus end is connected to a first end of the central body, a second end of the central body is connected to a first end of the C-shaped handle, and the handle end cap is connected to a second end of the C-shaped handle. Further, the method includes installing a rechargeable battery within the handle end cap, inserting a microcontroller within the central body, and operatively connecting the microcontroller to the rechargeable battery. Furthermore, the method includes forming a case to hold the elongate body and the therapeutic tablet and forming a charging port in the case. The charging port is configured to mate with the handle end cap. Moreover, the method includes installing an electromagnetic coil within the handle end cap and connecting the electromagnetic coil to the rechargeable battery. The electromagnetic coil is configured to generate a charging current when the handle end cap is placed adjacent to the charging port. In addition, the method includes installing a near field communications unit within the central body and operatively connecting the near field communications unit with the microcontroller. The method further includes linking a therapeutic tablet including a touch screen to the microcontroller. The therapeutic tablet includes a memory including program instructions including a hand therapy treatment plan and one or more processors configured to execute the program instructions to receive near field communications from the near field communications unit and display the hand therapy treatment plan and hand therapy exercises upon the touch screen. The hand therapy exercises are configured to direct a patient to write upon the touch screen with the stylus end while gripping the C-shaped handle. The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
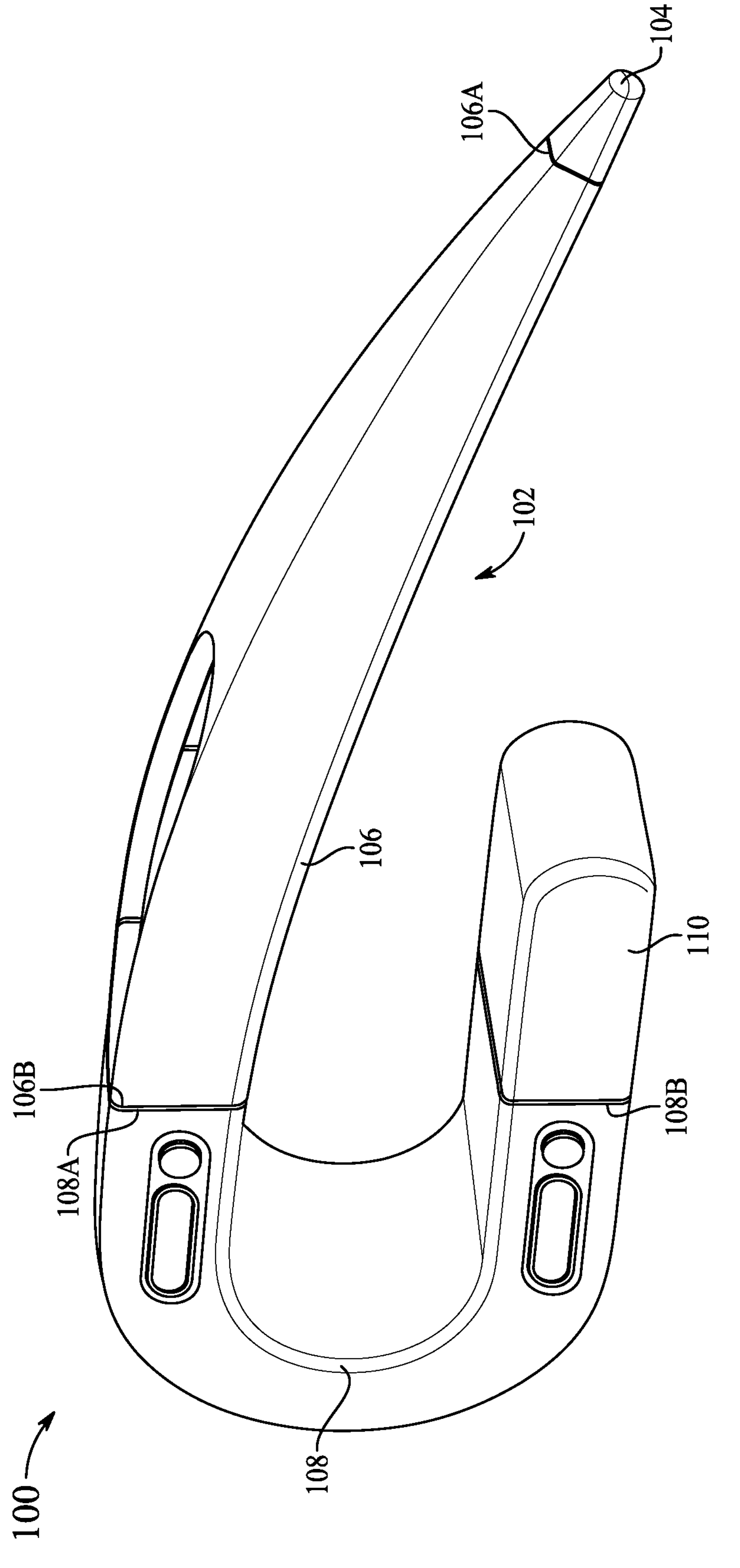
FIG. 1 is a schematic perspective view of a smart stylus for use in hand therapy, according to certain embodiments.

In the drawings, like reference numerals designate identical or corresponding parts throughout the several views. Further, as used herein, the words “a,” “an” and the like generally carry a meaning of “one or more”, unless stated otherwise.

Furthermore, the terms “approximately,” “approximate,” “about” and similar terms generally refer to ranges that include the identified value within a margin of 20%, 10%, or preferably 5%, and any values therebetween.

Aspects of this disclosure are directed to a system and a method for rehabilitation therapy of stroke affected limbs, in particular, paralyzed hands. The present disclosure includes a smart stylus, a smart stylus therapeutic system including the smart stylus and a therapeutic tablet, and a method describing the implementation of the smart stylus and the smart stylus therapeutic system. The system described in the present disclosure tracks the progress of a particular patient using the smart stylus in conjunction with the therapeutic system in order to personalize a plurality of parameters for a tailored experience and accelerated recovery of the particular patient. Further, the system described herein allows for remote goal setting and progress tracking of the particular patient. In addition, the system is capable of remote monitoring and tele-rehabilitation by one or more physicians.

Referring to FIG. 1, a schematic perspective view of a smart stylus 100 for use in hand therapy is illustrated. In particular, the smart stylus 100 is a near field communications (NFC) and Wi-Fi enabled device, with ergonomic design elements to support a patient in rehabilitation exercises and therapy through full recovery. The smart stylus 100 includes an elongate body 102 having a stylus end 104, a central body 106, a C-shaped handle 108, and a handle end cap 110. The central body 106 and the handle end cap 110 are slidably coupled to the C-shaped handle 108 to define the elongate body 102. The stylus end 104 is connected to a first end 106A of the central body 106. The first end 106A of the central body 106 is configured to detachably couple with the stylus end 104. As such, the stylus end 104 may be detached from the central body 106 and replaced as needed due to wear and tear after regular use of the smart stylus 100. Further, a second end 106B of the central body 106 is connected to a first end 108A of the C-shaped handle 108. The second end 106B of the central body 106 is configured to slidably couple with the first end 108A of the C-shaped handle 108, such that the central body 106 may extend away from the C-shaped handle 108 by a distance defined by a coupling mechanism provided between the central body 106 and the C-shaped handle 108. In some aspects, the central body 106 and the C-shaped handle 108 are made of elastomeric thermoplastic. In general, elastomeric thermoplastics are a class of copolymers or a physical mix of polymers that include materials with both thermoplastic (thermoset) and elastomeric (elastic) properties. As such, elastomeric thermoplastics possess an ability to stretch to moderate elongations and return to their near original shape to create a sustainable and reliable material. In addition, the C-shaped handle 108 provides a curved shape to the smart stylus 100, where the curved shape may enhance a functionality and performance of the smart stylus 100. A curvature of the curved shape provided by the C-shaped handle 108 is strategically designed to optimize a grip and control of the patient during occupational therapy exercises. Further, the curvature of the C-shaped handle provides an ergonomic grip to the patient, thereby reducing hand fatigue and discomfort, and also, improving usability, comfort, and continued usage of the smart stylus 100, during a therapy session. The curvature of the C-shaped handle 108 mimics a natural shape of a hand of the patient.

In some aspects, the central body 106 is configured to taper in width and depth from the second end 106B of the central body 106 to the first end 106A of the central body 106. The central body 106 is shaped in order to have a slimmer first end 106A as compared to the second end 106B. The central body 106 has a rounded edge rectangular cross-section having a width and a thickness that progressively decreases from the second end 106B to the first end 106A to couple with the stylus end 104. Further, the handle end cap 110 is connected to a second end 108B of the C-shaped handle 108. In particular, the handle end cap 110 is configured to detachably, and slidably, couple with the second end 108B of the C-shaped handle 108, as such, the handle end cap 110 may extend away from the C-shaped handle 108 by a distance defined by a coupling mechanism provided between the handle end cap 110 and the C-shaped handle 108.

Figure 2:
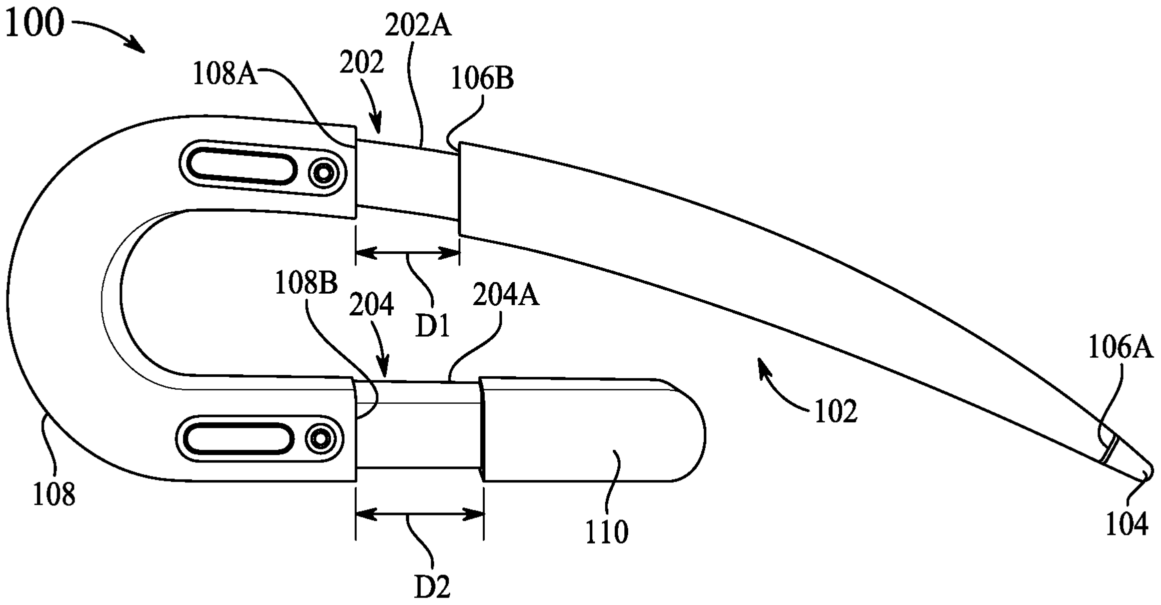
FIG. 2 is a schematic side view of the smart stylus of FIG. 1 showing an extended configuration thereof, according to certain embodiments.

Referring to FIG. 2, a schematic side view of the smart stylus 100 showing an extended configuration is illustrated. The extended configuration of the smart stylus 100 may be defined as an extended position at which both the central body 106 and the handle end cap 110 extend away from the C-shaped handle to increase an overall length of the smart stylus 100 as needed to adjust to different hand lengths. The extended configuration of the smart stylus 100 is defined by a first sliding mechanism 202 located between the central body 106 and the C-shaped handle 108 and a second sliding mechanism 204 located between the handle end cap 110 and the C-shaped handle 108. In particular, the first sliding mechanism 202 is located between the central body 106 and the first end 108A of the C-shaped handle 108. The first sliding mechanism 202 is slidably coupled with the central body 106 and the first end 108A of the C-shaped handle 108 in such a way that the central body 106 may move away from the C-shaped handle by a first distance 'D1'. As such, the overall length of the smart stylus 100 defined by the stylus end 104 and the C-shaped handle 108 at a normal position, otherwise known as a non-extended position, may increase by the first distance 'D1'. In one example, the first sliding mechanism 202 may include an extended portion 202A attached to the first end 108A of the C-shaped handle 108. The extended portion 202A may be configured to slidably receive within the second end 106B of the central body 106, as such, the central body 106 may slide over the extended portion 202A for the first distance 'D1'. Further, a stopping mechanism may be defined in the second end 106B of the central body 106 and the extended portion 202A to prevent movement of the central body 106 beyond the first distance 'D1' or to avoid detachment of the central body 106 from the extended portion 202A. Moreover, the first sliding mechanism 202 may include a locking mechanism to lock a position of the central body 106 at one or more places with the extended portion 202A such that the overall length of the smart stylus 100 may be fixed at different lengths per the hand size of the patient. In one example, a spring biased button may be coupled to the extended portion 202A, and multiple holes may be defined in the central body 106. Each of the holes may be configured to receive the spring biased button therethrough and defined at equal distance to define varying overall length for the smart stylus 100 based on the number of holes. During a locking position, the spring biased button may be engaged with one of the multiple holes at normal position thereof and to cause sliding of the central body 106 over the extended portion 202A, a force may be applied on the spring biased button to disengage from the hole. Upon releasing the force, the spring biased button is set in a preferred position by engaging with one of the multiple holes.

The smart stylus 100 further includes the second sliding mechanism 204 located between the second end 108B of the C-shaped handle 108 and the handle end cap 110. In particular, the second sliding mechanism 204 is slidably coupled with the handle end cap 110 and the second end 108B of the C-shaped handle 108 in such a way that the handle end cap 110 may move away from the C-shaped handle 108 by a second distance 'D2'. As such, an overall length of a handle portion of the smart stylus 100 defined by the handle end cap 110 and the C-shaped handle 108 at a normal position, otherwise known as a non-extended position, may increase by the second distance 'D2'. In one example, the second sliding mechanism 204 may include an extended portion 204A attached to the second end 108B of the C-shaped handle 108. The extended portion 204A may be configured to slidably receive within the handle end cap 110, as such, the handle end cap 110 may slide over the extended portion 204A for the second distance 'D2'. As described with reference to the first sliding mechanism 202, the second sliding mechanism 204 may include an identical stopping mechanism and locking mechanism. As such, a length of the elongate body 102 depends on an adjustment of the first sliding mechanism 202 and the second sliding mechanism 204. In particular, the first sliding mechanism 202 in collaboration with the second sliding mechanism 204 provides extension abilities to the smart stylus 100. In some aspects, the above mentioned extension abilities of the smart stylus 100 adjusts the smart stylus to a comfortable length for use by the patient.

Figure 3A:
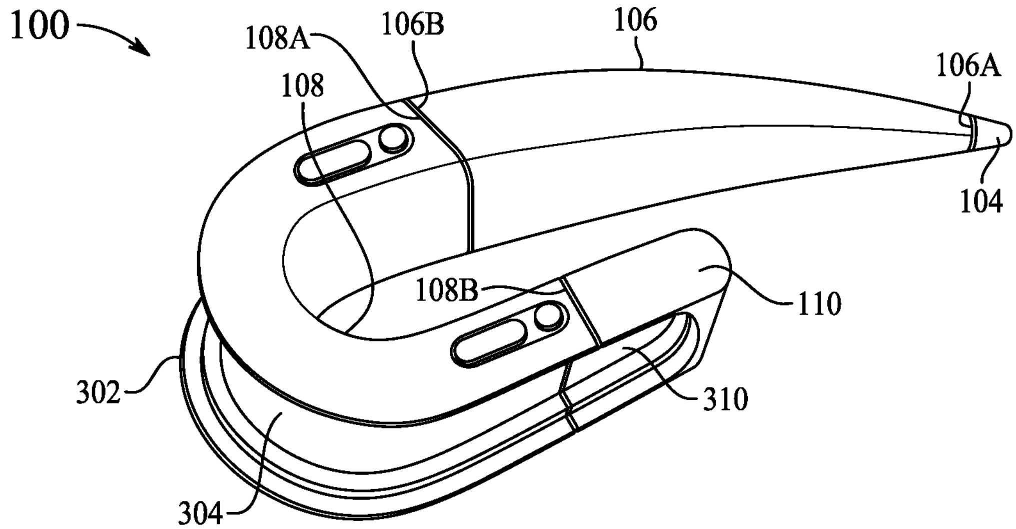
FIG. 3A is a schematic rear perspective view of the smart stylus of FIG. 1, according to certain embodiments.

Referring to FIG. 3A, a schematic rear perspective view of the smart stylus 100 is illustrated. As can be seen from FIG. 3A, an outer region 302 of the C-shaped handle 108 includes a first groove 304 which extends from the first end 108A of the C-shaped handle 108 to the second end 108B of the C-shaped handle 108. The outer region 302 of the C-shaped handle 108, included in the smart stylus 100, is configured to define the first groove 304 in order to allow a thumb or any one of the figures of the patient to rest inside the first groove 304 for better grip and comfort of the patient. In some aspects, the first groove 304 has a width in a range of 80% to 90% of a width of the C-shaped handle 108, and a depth in a range of 0.25 centimeters (cm) to 1.0 cm. In other aspects, the dimensional specifications such as the width and the depth of the first groove 304 may vary based on various factors including, but not limited to, an overall size of the C-shaped handle 108, material used for making the C-shaped handle 108, and use of the smart stylus 100 for patients such as adult patients or young patients.

Figure 3B:
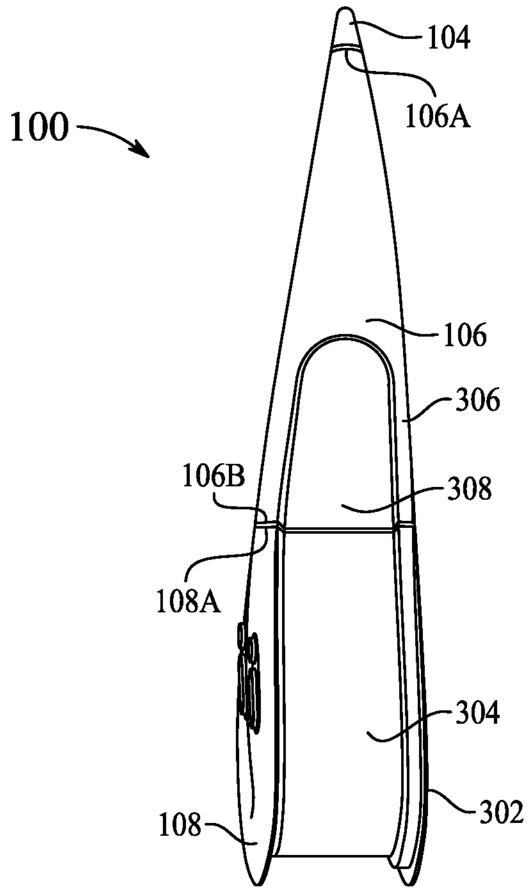
FIG. 3B is a schematic top view of the smart stylus of FIG. 1, according to certain embodiments.

Referring to FIG. 3B, a schematic top perspective view of the smart stylus 100 is illustrated. As can be seen from FIG. 3B, an outer region 306 of the central body 106 from the second end 106B of the central body 106 to about halfway between the first end 106A of the central body 106 and the second end 106B of the central body 106 includes a second groove 308 which matches the first groove 304 of the C-shaped handle 108 in depth and width. The second groove 308 is similar in dimensional specifications and constructional design to the first groove 304 to align with the first groove 304 when the central body 106 is slidably coupled to the C-shaped handle 108 using the first sliding mechanism 202. In some aspects, the first groove 304 and the second groove 308 are defined in the outer regions 302 and 306 of the C-shaped handle 108 and the central body 106, respectively, of the smart stylus 100 for improved grip and ergonomics of the smart stylus 100. Further, the first groove 304 and the second groove 308 may be defined as indents, to accommodate the thumb and one or more fingers of the patient, in the C-shaped handle 108 and the central body 106. In some aspects, a rough surface texture may be defined in the first and second grooves 304, 308 to further improve the gripping capabilities of the smart stylus 100. As shown in FIG. 3A, in some aspects of the present disclosure, a third groove 310 may be defined in the handle end cap 110 to match the first groove 304 in depth and width. The third groove 310 is similar in dimensional specifications and constructional design to the first groove 304 to align with the first groove 304 when the handle end cap 110 is slidably coupled to the C-shaped handle 108 using the second sliding mechanism 204. The third groove 310 is defined in the handle end cap 110 for improved grip by accommodate the thumb or one or more fingers of the patient.

Figure 4A:
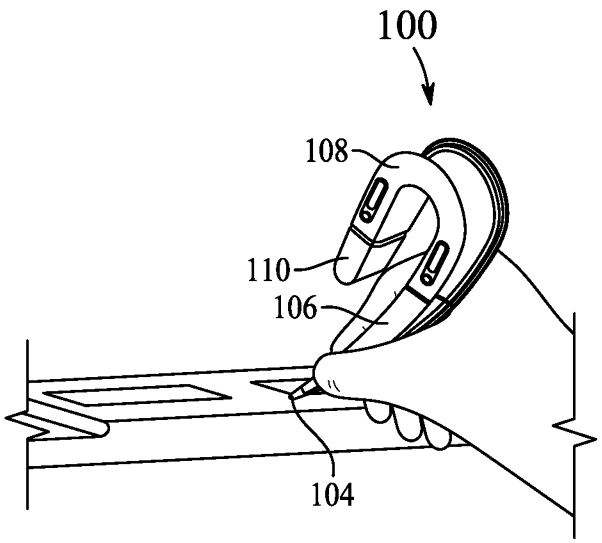
FIG. 4A depicts use of the smart stylus, according to certain embodiments.
Figure 4B:
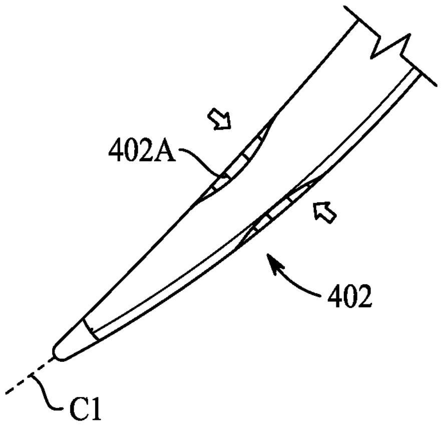
FIG. 4B is a schematic enlarged view of a portion of the smart stylus showing a first flexible grip, according to certain embodiments.
Figure 4C:
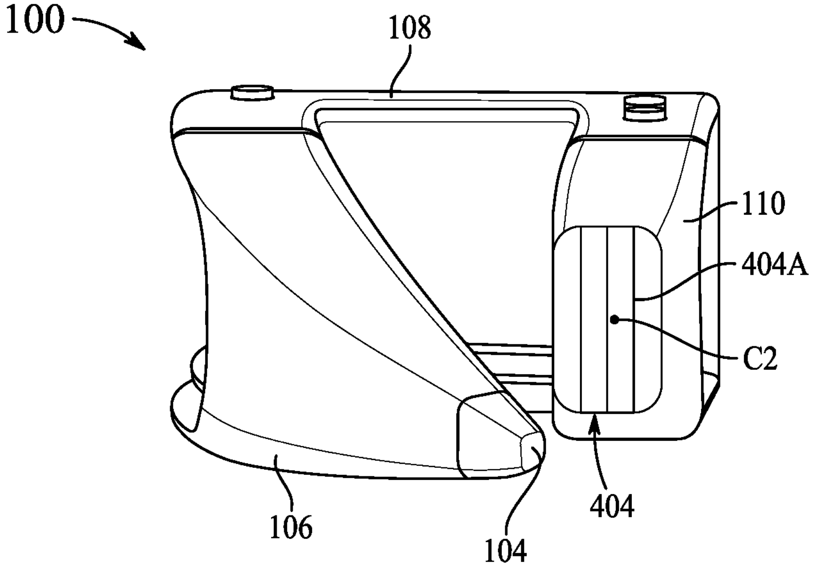
FIG. 4C is a schematic perspective of the smart stylus showing a second flexible grip, according to certain embodiments.

Referring to FIG. 4A, a schematic perspective view of the smart stylus 100 depicting hand holding thereof is illustrated. In some aspects, the smart stylus 100 is a flexible device which allows the patient to control an amount of pressure applied thereon based on an ability of the patient. Referring to FIG. 4B, a schematic diagram of an enlarged view of the central body 106 of the smart stylus 100 showing a first flexible grip 402 is illustrated, according to certain aspects. In particular, the smart stylus 100 includes the first flexible grip 402 located on the central body 106 halfway between the first end 106A of the central body 106 and the second end 106B of the central body 106. In some aspects, the first flexible grip 402 includes raised lines 402A extending across the central body 106 perpendicular to a central axis 'C1' of the central body 106. In one example, the raised lines 402A may extend along the thickness of the central body 106. In another example, the raised lines 402A may extend along the width of the central body 106. In particular, the first flexible grip 402 having the raised lines 402A is employed to provide an anti-slip grip to the patient when holding the smart stylus 100. In addition, the first flexible grip 402 may provide flexibility and pressure moderation abilities, while performing a task with the stylus end 104 of the smart stylus 100. Referring to FIG. 4C, a schematic diagram of the smart stylus 100 showing a second flexible grip 404 is illustrated, according to certain aspects. In particular, the smart stylus 100 includes the second flexible grip 404 located on the handle end cap 110, wherein the second flexible grip 404 includes raised lines 404A extending across the handle end cap 110 perpendicular to a central axis 'C2' of the handle end cap 110. In one example, the raised lines 404A may extend along a thickness of the handle end cap 110. In another example, the raised lines 402A may extend along a width of the handle end cap 110. In yet another example, the raised lines 404A may be defined at an end of the handle end cap 110 along the thickness or the width thereof. The first flexible grip 402 and the second flexible grip 404 may assist the patient in improving grip strength as well as cognitive control of the pressure applied on the smart stylus 100 while performing a task.

Figure 5A:
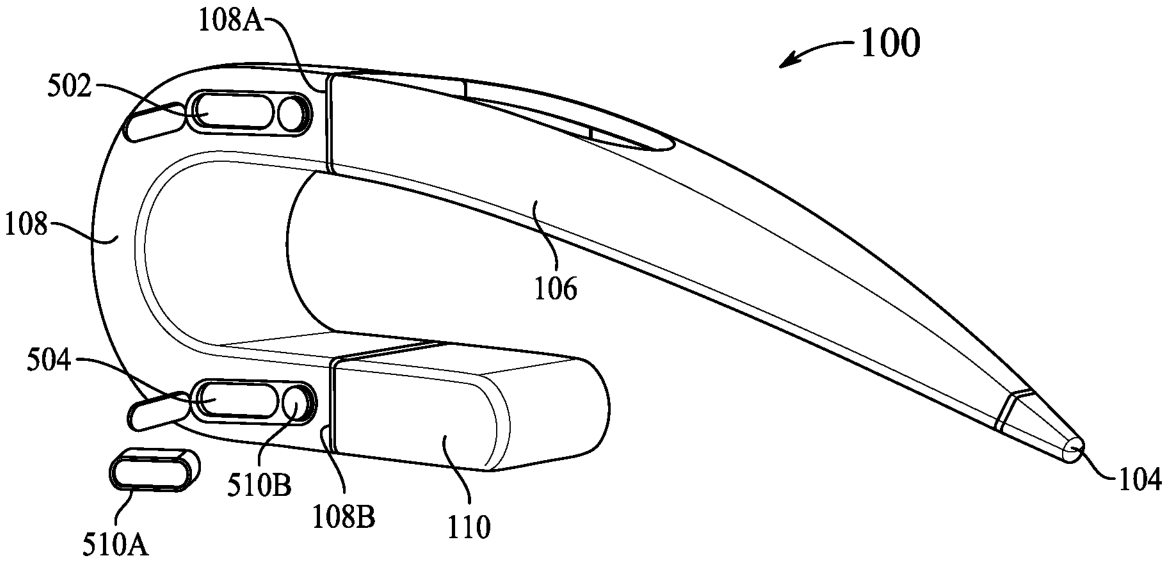
FIG. 5A is a schematic perspective view of the smart stylus showing weight receiving compartments, according to certain embodiments.

Referring to FIG. 5A, a schematic perspective view of the smart stylus 100 is illustrated. In one aspect of the present disclosure, the smart stylus 100 includes at least one upper weight receiving compartment 502. The upper weight receiving compartment 502 is defined at the first end 108A of the C-shaped handle 108. In another aspect of the present disclosure, the smart stylus 100 includes at least two upper weight receiving compartments 502. The at least two weight receiving compartments 502 further include a first upper weight receiving compartment and a second upper weight receiving compartment. As such, each upper weight receiving compartment 502 is located on either side of the C-shaped handle 108 near the first end 108A of the C-shaped handle 108. In one aspect of the present disclosure, the smart stylus 100 includes at least one lower weight receiving compartment 504. The lower weight receiving compartment 504 is defined at the second end 108B of the C-shaped handle 108. In another aspect of the present disclosure, the smart stylus 100 includes at least two lower weight receiving compartments 504. The lower weight receiving compartments 504 further include a first weight receiving compartment and a second weight receiving compartment. As such, each lower weight receiving compartment 504 is located on either side of the C-shaped handle 108 near the second end 108B of the C-shaped handle 108.

Figure 5B:
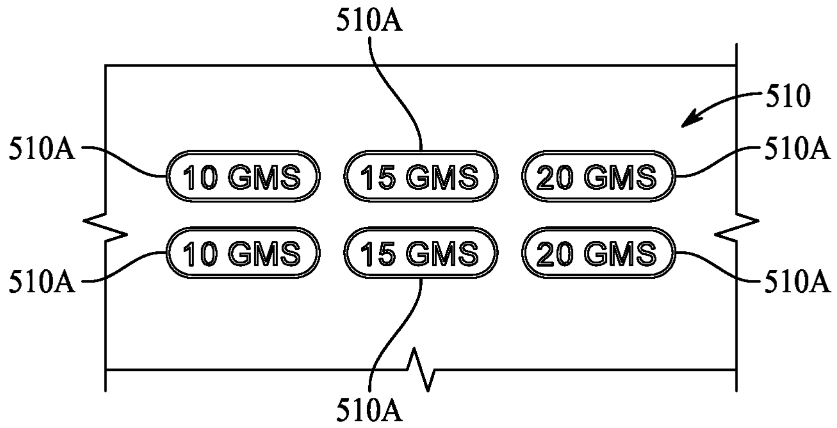
FIG. 5B is a schematic diagram of a plurality of weights associated with the smart stylus, according to certain embodiments.

Referring to FIG. 5B, a schematic diagram of a plurality of weights 510 is illustrated, according to certain aspects. In particular, each weight of the plurality of weights 510 is sized to fit within a respective weight receiving compartment. The respective weight receiving compartment refers to the upper and lower weight receiving compartments 502, 504. The upper weight receiving compartments 502 are configured to be hollow and structurally reinforced portion to securely house one or more of the plurality of weights 510. Similarly, the lower weight receiving compartments 504 are configured to be hollow and structurally reinforced portions to securely house one or more of the plurality of weights 510. In an example, the plurality of weights 510 includes, but are not limited to, one or more first weights weighing 10 grams, one or more second weights weighing 15 grams, and one or more third weights weighing 20 grams. In some aspects, as shown in FIG. 5A, the plurality of weights 510 includes an oblong weight 510A and a cylindrical weight 510B. The oblong weight 510A may have a cuboid shape and be configured to fit within the respective weight receiving compartments. Similarly, the cylindrical weight 510B may have a cylinder shape and be configured to fit within the respective weight receiving compartments. In particular, each side of the C-shaped handle 108 includes a weight receiving compartment sized to receive the oblong weight 510A and a weight receiving compartment sized to receive the cylindrical weight 510B. Each weight receiving compartment may include retention features to hold a respective weight within the weight receiving compartment. In a non-limiting example, the retention features may include indentations in the sides of the weight receiving compartment configured to grip the weight. In another non-limiting example, the weights may have corresponding features, such as raised bands which are configured to fit within the indentations. In another non-limiting example, the weight receiving compartment may have a door as shown connected to 502 in FIG. 5A to cover the weight receiving compartment 502. Weight receiving compartment 504 may also have a door, as shown in FIG. 5A.

Figure 5C:
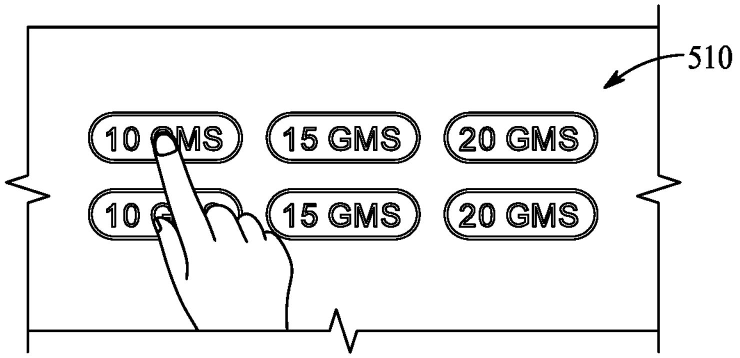
FIG. 5C depicts a schematic illustration of a method of removing the plurality of weights, according to certain embodiments.
Figure 5D:
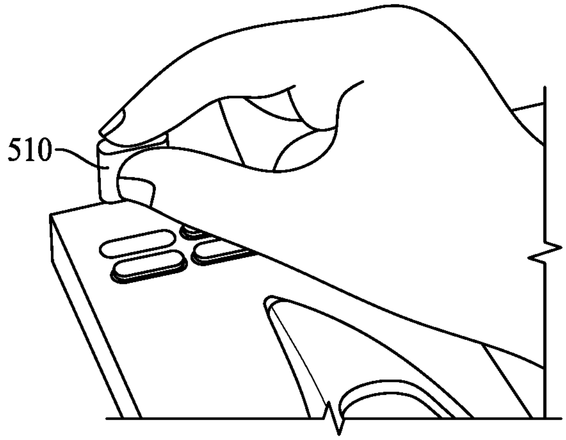
FIG. 5D depicts a schematic illustration of the method of FIG. 5C showing removal of one weight from the plurality of weights, according to certain embodiments.

Referring to FIG. 5C and FIG. 5D, schematic illustrations of a method of removing one or more of the plurality of weights 510 from weight receiving slots defined in a case is depicted. In some aspects, the plurality of weights 510 may be removed manually, and installed manually in the upper and lower weight receiving compartments 502, 504 of the smart stylus 100. The plurality of weights 510 are included in order to keep the patient from hitting a therapeutic plateau during rehabilitation phase. More particularly, a therapeutic plateau refers to a stagnancy in a course of recovery of the patient. In some cases, when certain parameters such as, but are not limited to, weight of a therapeutic instrument, and a style of a therapeutic program are not varied sufficiently, the patient may reach at the therapeutic plateau, hindering the patient from further rehabilitation. When subjected to dissimilar therapeutic techniques, the brain of the patient may halt formation of new neural pathways, which are essential for continued rehabilitation. In an example, the plurality of weights 510 are placed within the weight receiving compartments in such a way that a top end of the weight 510 projects above a top surface of the case so that the patient can easily remove the plurality of weights 510 from the case.

In another example, an indent or a raised portion may be defined at the top end of the plurality of weights 510 to comfortably hold the plurality of weights 510 while removing the plurality of weights 510 from the weight receiving slots.

Figure 6A:
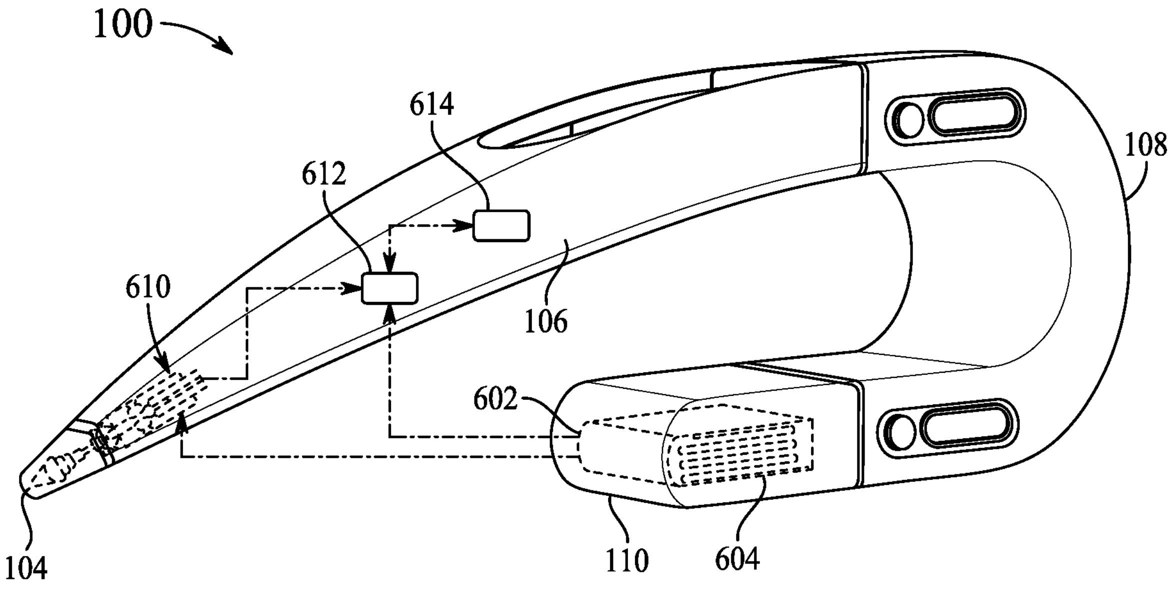
FIG. 6A is a schematic perspective view of the smart stylus depicting one or more internal electrical components thereof, according to certain embodiments.
Figure 6B:
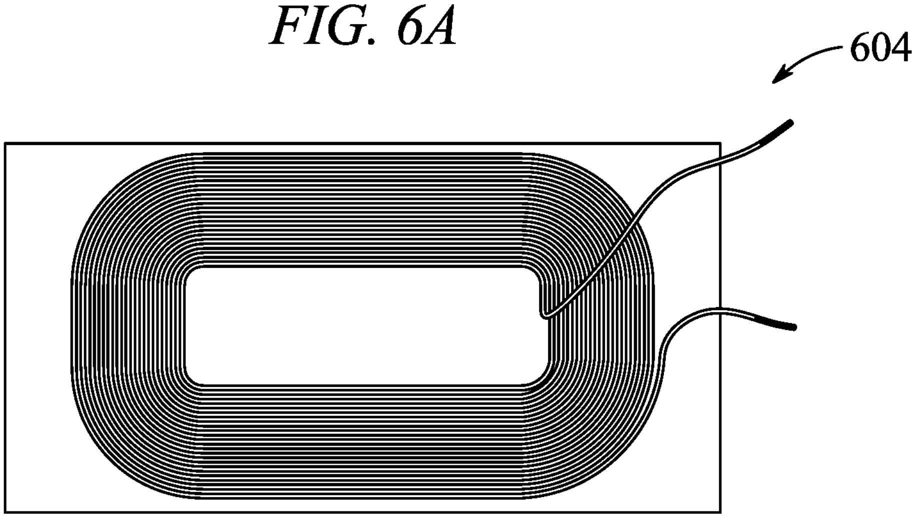
FIG. 6B is a schematic diagram of an electromagnetic coil located in the smart stylus, according to certain embodiments.
Figure 6C:
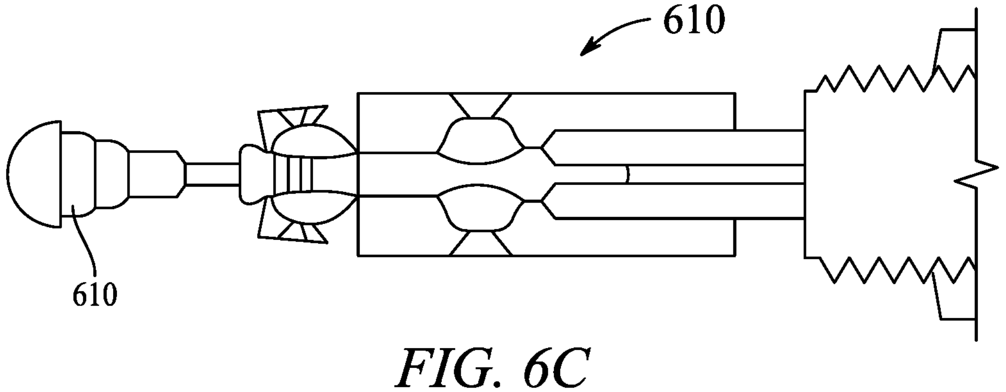
FIG. 6C is a schematic diagram of a pressure sensor located in the smart stylus, according to certain embodiments.

Referring to FIG. 6A, a schematic perspective view of the smart stylus 100 showing one or more internal components is illustrated, according to certain aspects. The smart stylus 100 includes a rechargeable battery 602 located within the handle end cap 110. In an example, the rechargeable battery 602 may be equipped with wireless charging technology and supports normal functioning of the smart stylus 100. In some aspects, the rechargeable battery 602 may be a lithium-ion battery, a lithium-polymer battery, a nickel-cadmium battery, and the like. The handle end cap 110 is configured to have sufficient space in order to accommodate the rechargeable battery 602. Further, referring to FIG. 6B, a schematic illustration of an electromagnetic coil 604 is depicted, according to certain aspects. In particular, the smart stylus 100 includes the electromagnetic coil 604 for wireless charging of the rechargeable battery 602. The electromagnetic coil 604 may be made of copper (Cu), or any other suitable ferrite material. Furthermore, referring to FIG. 6C, a schematic illustration of a pressure sensor 610 is depicted, according to certain aspects. In particular, the rechargeable battery 602 is electrically coupled with the pressure sensor 610 located within the elongate body 102. The pressure sensor 610 is further connected to the stylus end 104. The pressure sensor 610 is configured to generate an electric signal indicative of an amount of pressure applied on the stylus end 104 by the patient when the smart stylus 100 is in use. Further, the pressure sensor 610 is configured to communicate with the rechargeable battery 602 to receive operating power therefrom. Though FIG. 6C illustrates a specific construction of the pressure sensor 610, any other known pressure sensor adaptable to the smart stylus 100 may be implemented for the purpose of detecting the amount of pressure applied on the smart stylus 100 by the patient. Moreover, as can be seen in FIG. 6A, the smart stylus 100 includes a microcontroller 612 located within the central body 106. In some aspects, the microcontroller 612 is operatively connected to the rechargeable battery 602 and the pressure sensor 610. The microcontroller 612 is configured to communicate with the pressure sensor 610 to receive the electric signal indicative of the amount of pressure applied on the smart stylus 100. Upon receiving the electric signal, the microcontroller 612 may be configured to determine a pressure value and the pressure value may be further stored in a memory of the microcontroller 612 for further reference or use. The microcontroller 612 is configured to communicate with the rechargeable battery 602 to control charging of the rechargeable battery 602. In some aspects, the smart stylus 100 includes a near field communications unit 614 located within the central body 106 and operatively connected with the microcontroller 612. In some aspects, an additional rechargeable battery may be located with the central body 106 to power the pressure sensor 610, the microcontroller 612, and the near field communications unit 614. The additional rechargeable battery may be charged using the wireless charging technology. The electrical connection among the rechargeable battery 602, the pressure sensor 610, the microcontroller 612, and the near field communications unit 614 are shown schematically in FIG. 6A by broken lines. In general, near field communication (NFC) is a set of communication protocols that provides communication between two electronic devices over a distance of 4 centimeters or less. NFC offers a low-speed connection through a simple setup that may be used for the bootstrapping of capable wireless connections. Similar to other proximity card technologies, NFC is based on inductive coupling between two electromagnetic coils present on a NFC-enabled device such as a tablet. NFC communicating in one or both directions uses a frequency of 13.56 MHz in the globally available unlicensed radio frequency ISM band, compliant with the ISO/IEC 18000-3 air interface standard at data rates ranging from 106 to 848 kbit/s. In some aspects of the present disclosure, the near field communications unit 614 may be included in order to send a set of data from the smart stylus 100 to a plurality of devices present in a vicinity of the smart stylus 100. In some aspects of the present disclosure, the near field communications unit 614 may be included in order to receive another set of data from the plurality of devices present in the vicinity of the smart stylus 100. Further, the microcontroller 612 is configured to be operatively and electrically coupled with the rechargeable battery 602, the pressure sensor 610, and the near field communications unit 614. In a non-limiting example, the near field communications unit 614 may use a Bluetooth protocol.

Figure 7A:
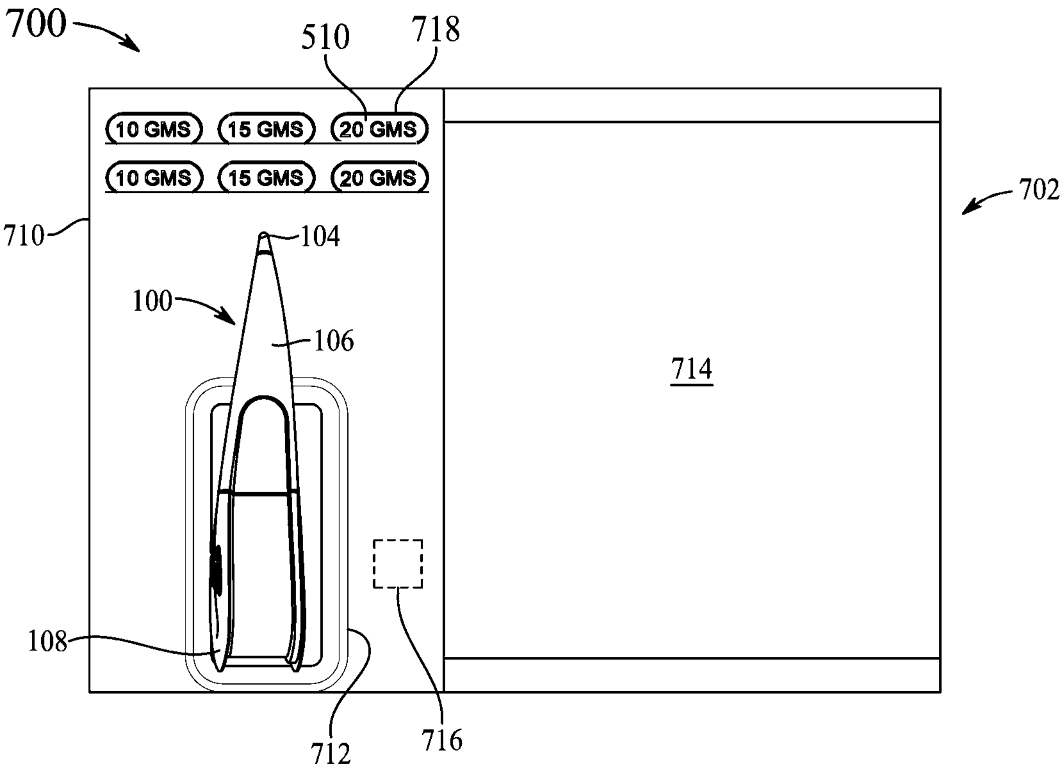
FIG. 7A is a schematic diagram of a smart stylus therapeutic system for use in hand therapy, according to certain embodiments.

Referring to FIG. 7A, a smart stylus therapeutic system 700 for use in hand therapy is illustrated, according to certain aspects. The smart stylus therapeutic system 700 is alternatively referred to as 'the system 700' for brevity in explanation. The system 700 refers to the smart stylus 100 in conjunction with a therapeutic tablet 702 for use in the hand therapy, such as, hand rehabilitation and movement restoration after a stroke. In some aspects, the system 700 includes the smart stylus 100 including the elongate body 102 having the stylus end 104. Further, the smart stylus 100 includes the central body 106, the C-shaped handle 108, and the handle end cap 110. As such, the stylus end 104 is connected to the first end 106A of the central body 106, the second end 106B of the central body 106 is connected to the first end 108A of the C-shaped handle 108. Furthermore, the handle end cap 110 is connected to the second end 108B of the C-shaped handle 108. The system 700 further includes the rechargeable battery 602 located within the handle end cap 110. In addition, the system 700 includes the microcontroller 612 located within the central body 106 and the microcontroller 612 is operatively connected to the rechargeable battery 602. The system 700 further includes the near field communications unit 614 located within the central body 106 and operatively connected with the microcontroller 612.

The system 700 includes a case 710. The case 710 is configured to hold the elongate body 102, in particular the smart stylus 100, and the therapeutic tablet 702. In some aspects, the case 710 includes a charging port 712 configured to mate with the handle end cap 110 of the smart stylus 100. In addition, the system 700 includes the electromagnetic coil 604 located within the handle end cap 110 and connected to the rechargeable battery 602. As such, the electromagnetic coil 604 is configured to generate a charging current when the handle end cap 110 is placed adjacent to the charging port 712. In particular, the charging port 712 is a wireless charging station, providing the smart stylus 100 of the system 700 with wireless charging capabilities, and the electromagnetic coil 604 present in the handle end cap 110 is configured to receive the charging current from the charging port 712. In an aspect, the charging port 712 is defined as an engraved slot in the case 710 having a size and shape identical to the shape and size of the handle end cap 110 such that the handle end cap 110 may be received within the charging port 712 for charging the smart stylus 100 In some aspects, a voltage, and an ampere of the charging current may be predetermined based on safety and performance parameters. In some aspects, the charging port 712 may have a temperature sensors in order to detect heat generated during the charging of the smart stylus 100 and protect the system 700 from overheating during the charging process.

In some aspects, the system 700 includes the therapeutic tablet 702 equipped with a touch screen 714. The therapeutic tablet 702 includes a memory 716 for storing program instructions including a hand therapy treatment plan. Further, the therapeutic tablet 702 includes one or more processors configured to execute the program instructions to receive near field communications from the near field communications unit 614.

The smart stylus 100 of the system 700 includes the at least two upper weight receiving compartments 502, and each upper weight receiving compartment of the at least two upper weight receiving compartments 502 is located on either side of the C-shaped handle 108 near the first end 108A thereof. In addition, the smart stylus 100 of the system 700 includes the at least two lower weight receiving compartments 504, and each lower weight receiving compartment of the at least two lower weight receiving compartments 504 is located on either side of the C-shaped handle 108 near the second end 108B. Further, the system 700 includes the plurality of weights 510, each weight of the plurality of weights 510 is sized to fit within the respective weight receiving compartments. In some aspects, the plurality of weights 510 is stored in weight receiving slots 718 defined in the case 710. The case 710 is configured to define the weight receiving slots 718 on top left corner of the case 710. The weight receiving slots 718 are crafted with precision in order to suit the dimensional specifications and constructional details of the plurality of weights 510.

Figure 7B:
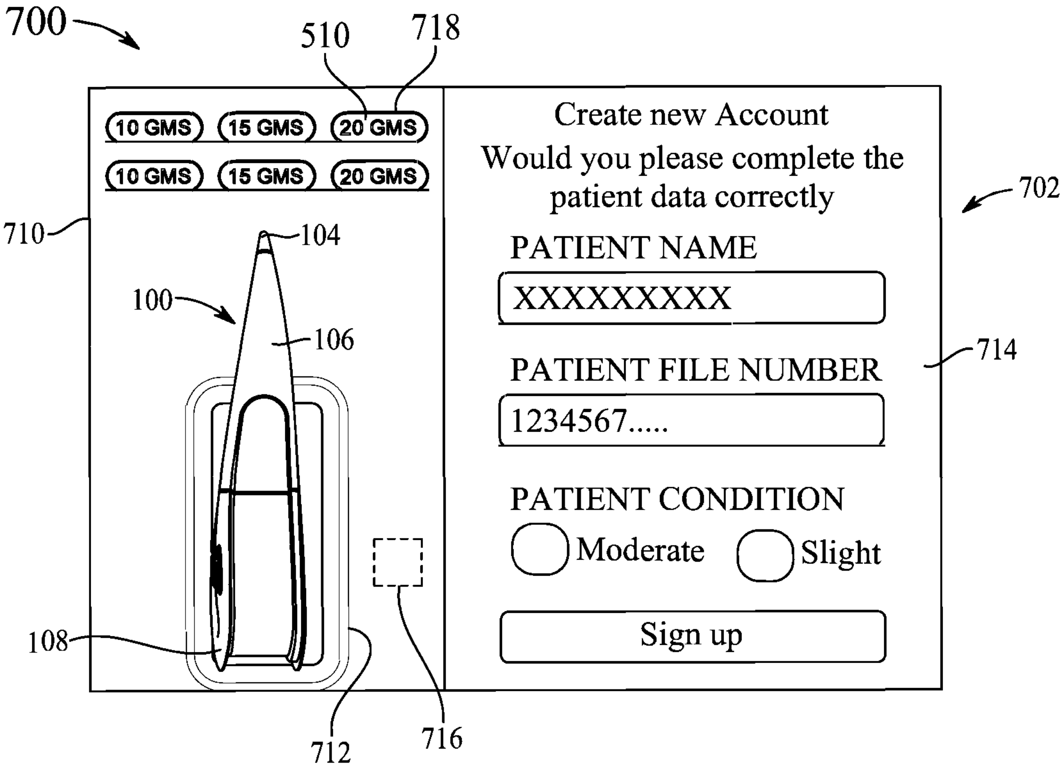
FIG. 7B is a schematic illustration of a program instruction displayed on a touch screen of the smart stylus therapeutic system, according to certain embodiments.
Figure 7C:
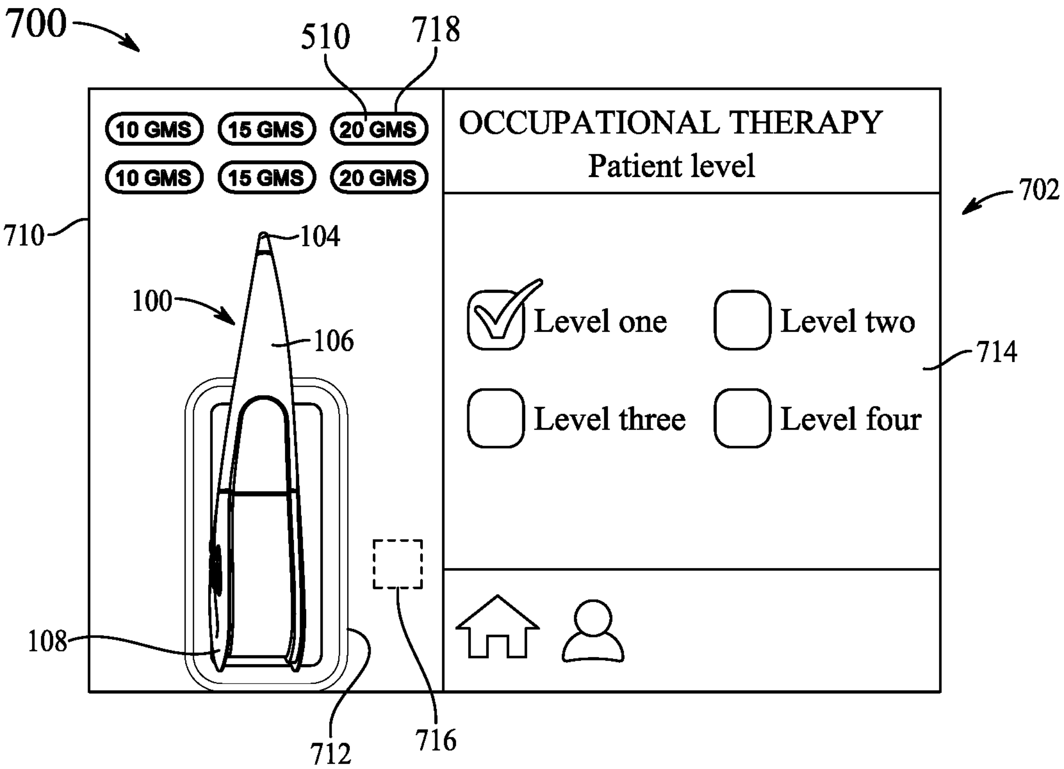
FIG. 7C is a schematic illustration of another program instruction displayed on the touch screen of the smart stylus therapeutic system, according to certain embodiments.

Referring to FIG. 7B, a schematic illustration of a program instruction on the touch screen 714 of the therapeutic tablet 702 is illustrated, according to certain aspects. The touch screen 714 prompts a set of instructions asking the patient to register and create an account. The account may be used to track the progress of the patient over time. Further, referring to FIG. 7C, a schematic illustration of another program instruction displayed on the touch screen 714 is illustrated, according to certain aspects. The program instructions as executed by the one or more processors displays a selection of tasks for the patient or physical therapist to select and proceed accordingly.

Figure 7D:
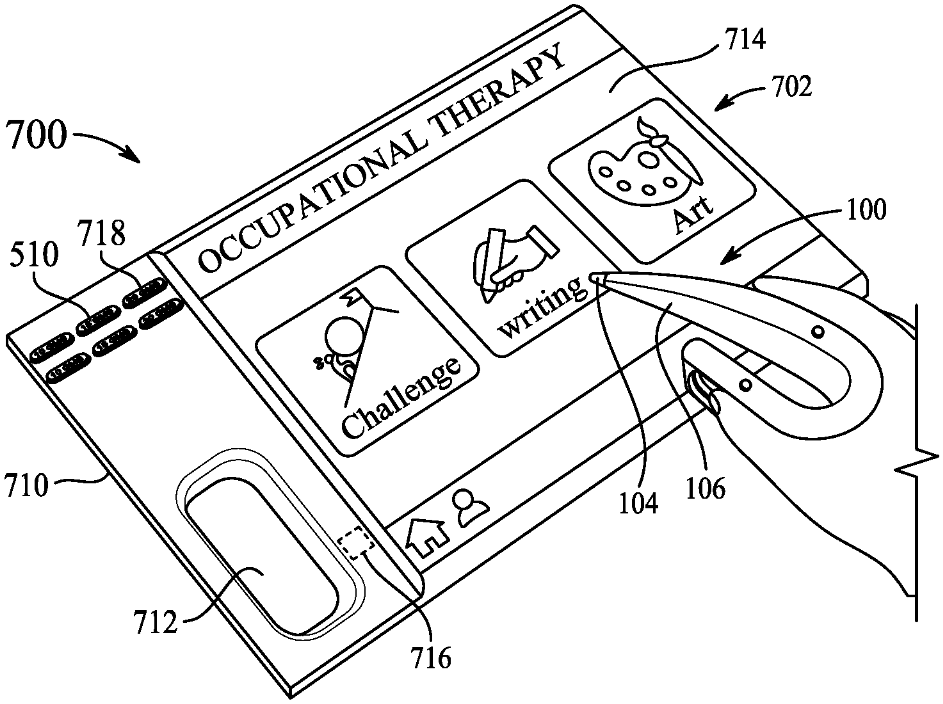
FIG. 7D is a schematic illustration of yet another program instruction displayed on the touch screen of the smart stylus therapeutic system, according to certain embodiments.

Referring to FIG. 7D, a schematic illustration of the touch screen 714 displaying the hand therapy treatment plan is illustrated. In particular, the program instructions as included in the therapeutic tablet 702, when executed by the one or more processors, display the hand therapy treatment plan and hand therapy exercises upon the touch screen 714. The hand therapy exercises are configured to direct the patient to write upon the touch screen 714 with the stylus end 104 while gripping the C-shaped handle 108. In some aspects, the patient may grip the smart stylus 100 of the system 700 with the first and the second flexible grips 402, 404.

Figure 8A:
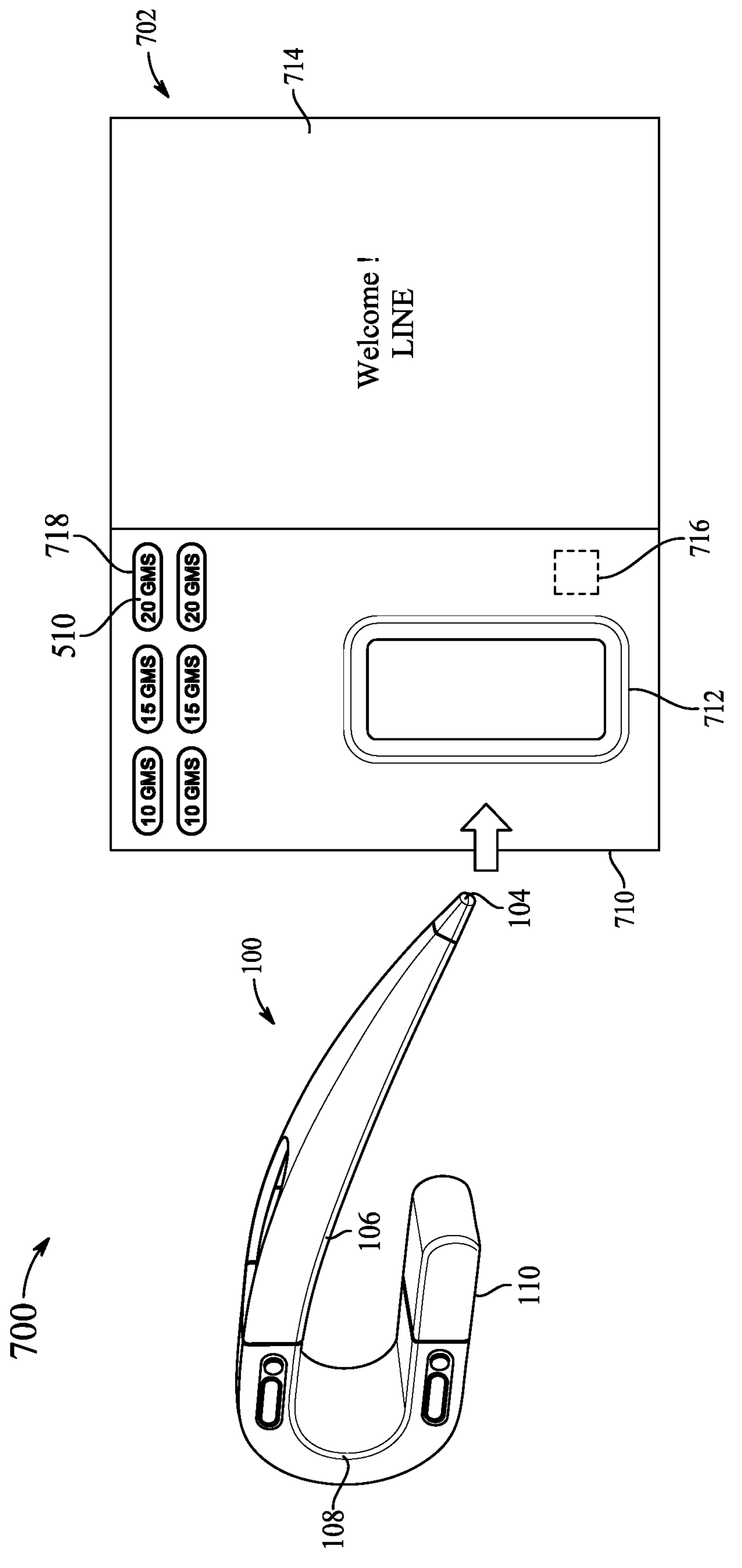
FIG. 8A is a schematic diagram of the smart stylus therapeutic system with the smart stylus detached from a therapeutic tablet, according to certain embodiments.
Figure 8B:
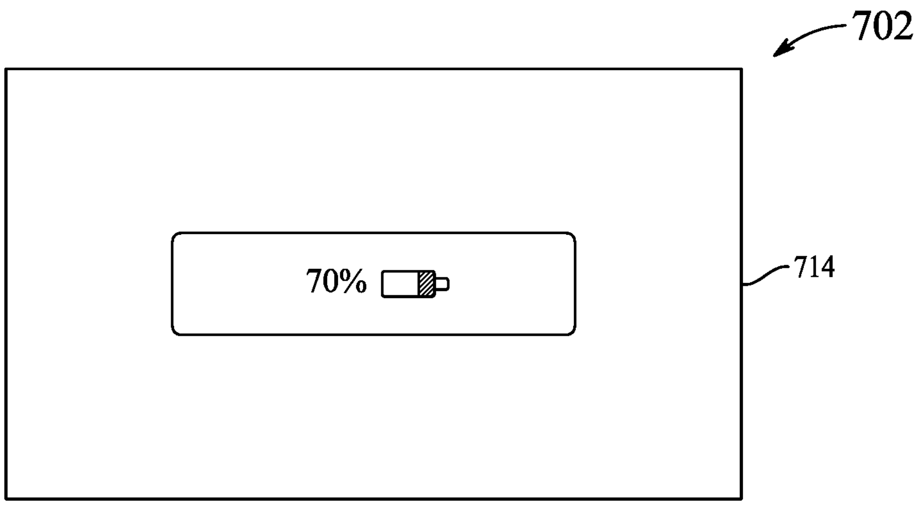
FIG. 8B is a schematic illustration of a battery charge status as displayed on the touch screen of the therapeutic tablet, according to certain embodiments.

Referring to FIG. 8A and FIG. 8B, schematic illustrations of the system 700 and the therapeutic tablet 702 are illustrated, according to certain aspects. As can be seen from FIG. 8A, the smart stylus, weights, charger and therapeutic tablet are held in a single unit. As can be seen from FIG. 8B, the therapeutic tablet 702 is configured to receive a battery charge status by the near field communications from the microcontroller 612 and display the battery charge status on the touch screen 714. The touch screen 714 of the therapeutic tablet 702 displays the battery charge status of the rechargeable battery 602 present in the handle end cap 110 of the smart stylus 100, in order to keep the patient updated of the battery charge status for the smart stylus 100. In some aspects, the therapeutic tablet 702 and the touch screen 714 may show an alert if the battery charge status is low and alert the patient to charge the smart stylus 100 as required. Further, the smart stylus 100 of the system 700 includes the pressure sensor 610 located within the elongate body 102 and connected to the stylus end 104. In particular, the pressure sensor 610 is connected to the microcontroller 612, as such, the pressure sensor 610 is configured to generate electrical signals in response to the amount of pressure sensed by the pressure sensor 610 when the stylus end 104 contacts the touch screen 714. In general, pressure sensors are devices that translate a magnitude of a physical pressure that is being exerted on the pressure sensor 610 into an output signal that may be used to establish a quantitative value for the pressure. In some aspects, the pressure sensor 610 may be including, but not limited to, potentiometric pressure sensors, inductive pressure sensors, capacitive pressure sensors, piezoelectric pressure sensors, strain gauge pressure sensors, variable reluctance pressure sensors, or a combination thereof.

The microcontroller 612 is configured to transmit the electrical signals related to the amount of pressure by near field communications to the therapeutic tablet 702. In other words, a magnitude of the pressure sensed by the pressure sensor 610 is determined and transmitted to the therapeutic tablet 702 by the near field communications unit 614. The therapeutic tablet 702 makes it easy for the patient to read and understand pressure readings, as recorded by the pressure sensor 610. In addition, the therapeutic tablet 702 is configured to receive the electrical signals related to the amount of pressure of the stylus end 104 against the touch screen 714 and select a weight from the plurality of weights 510 in accordance with the hand therapy treatment plan. The system 700 has the ability to determine appropriate weight amount, via the hand therapy treatment plan, for a particular patient depending on where the patient is in terms of progress pertaining to the hand therapy treatment plan. In some aspects, a dynamic approach of weight selection keeps the patient from hitting therapeutic plateau during the hand therapy. In some aspects, the hand therapy exercises include grip strength exercises, hand-eye coordination exercises, and interactive games configured to improve the motor skills, coordination, and cognitive functions. In some aspects, the hand therapy exercises may be remotely updated via a software application and additional exercises may be added to the existing hand therapy exercises in order to better suit the patient and therapeutic requirements.

Figure 8C:
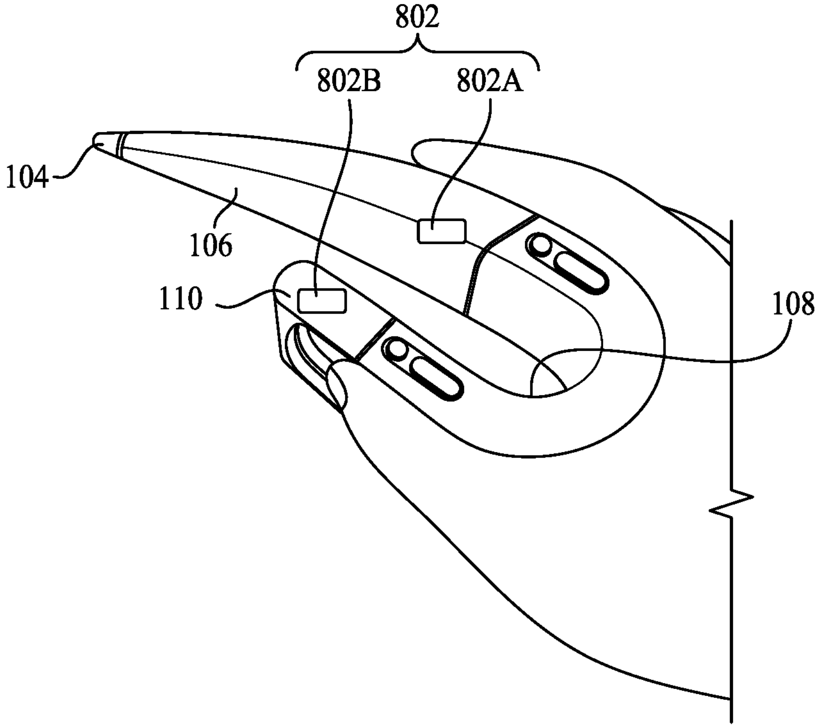
FIG. 8C is a schematic diagram of the smart stylus depicting a pair of proximity sensors, according to certain embodiments.

Referring to FIG. 8C, a schematic diagram of the smart stylus 100 having one or more proximity sensors 802 is illustrated, according to certain aspects. The one or more proximity sensors 802 may further include a first proximity sensor 802A and a second proximity sensor 802B. In particular, the first proximity sensor 802A is configured to be placed near a center of the central body 106 of the smart stylus 100. The second proximity sensor 802B is configured to be placed near a distal end of the handle end cap 110. The first proximity sensor 802A and the second proximity sensor 802B are configured to measure a distance between the center of the central body 106 and the distal end of the handle end cap 110. Further, the one or more proximity sensors 802 are electrically and operatively coupled with the rechargeable battery 602. In some aspects, sensor data collected by the one or more proximity sensors 802 is communicated to the microcontroller 612, and subsequently relayed on to the therapeutic tablet 702. In particular, shrinking of the distance between the proximity sensors of the smart stylus 100 due to the pressure applied by the patient may be determined by the first and second proximity sensors 802A, 802B. The distance readings between the central body 106 and the distal end of the handle end cap 110 may provide additional information required by the one or more physicians in order to develop a better rehabilitation therapy plan for the patient. In some aspects, the therapeutic tablet 702 may be connected with the microcontroller 612 via a Wi-Fi connection, an LTE connection, a mobile application platform, a website platform, or a combination thereof.

Figure 9:
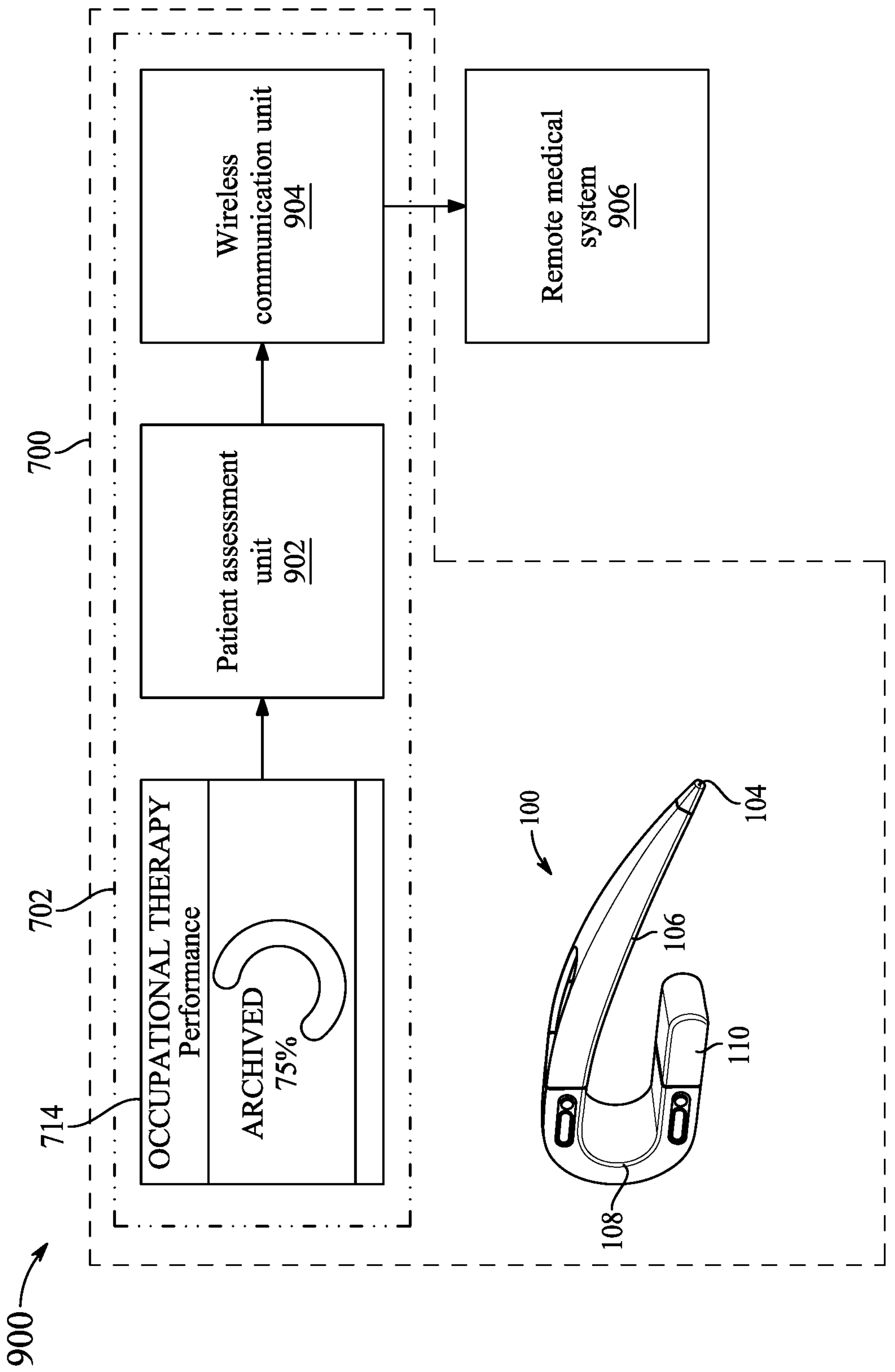
FIG. 9 is a schematic block diagram of a patient assessment computing environment, according to certain embodiments.

Referring to FIG. 9, a schematic block diagram of a patient assessment computing environment 900 is illustrated, according to certain aspects. In particular, the system 700 includes a patient assessment unit 902 located within the therapeutic tablet 702. The patient assessment unit 902 is configured to monitor a progress of the patient against a baseline assessment and generate a progress report. Further, the system 700 includes a wireless communication unit 904 located within the therapeutic tablet 702. The wireless communication unit 904 is configured to wirelessly transmit the progress report to a remote medical system 906 configured to monitor the progress of the patient. The progress of the patient is tracked throughout the hand therapy process, and a progress report is generated based on the baseline assessment of the patient. The baseline assessment refers to the assessment of the motor skills, hand-eye coordination, and cognitive skills of the patient conducted before the enrollment of the patient into the hand therapy. In respect to the baseline assessment, the progress report is tracked and sent to the remote medical system 906, where one or more healthcare professionals further examine the progress report of the patient. The remote medical system 906 is an integral part of the system 700 in order to make the hand therapy dynamic, adaptive and effective in developing new neural pathways in the brain of the patient.

Figure 10:
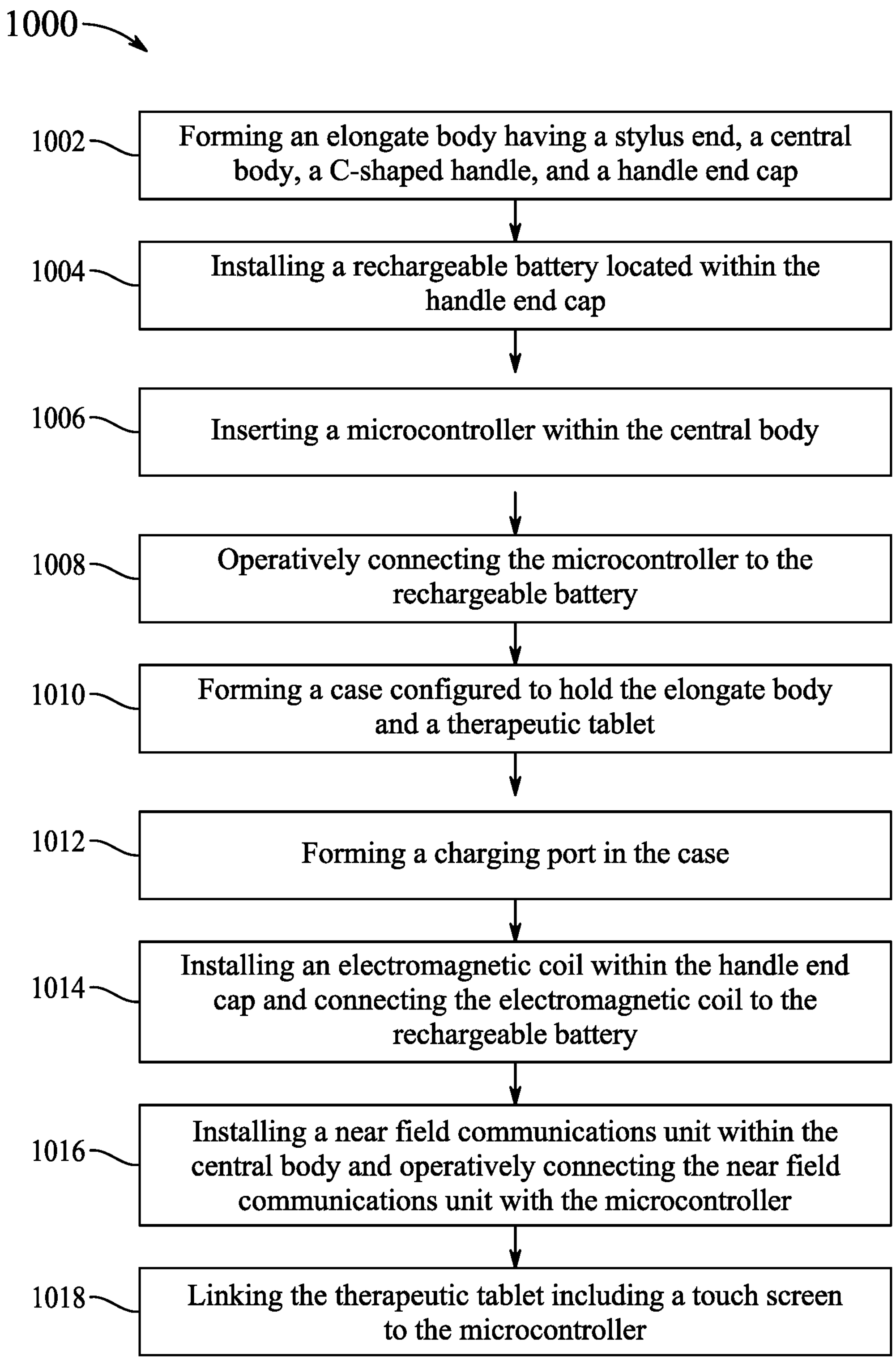
FIG. 10 is an exemplary flowchart of a method of using the smart stylus in the hand therapy, according to certain embodiments.

Referring to FIG. 10, a flowchart depicting a method 1000 of using the smart stylus 100 in hand therapy is illustrated, according to certain aspects. The order in which the method 1000 is described is not intended to be construed as a limitation, and any number of the described method steps may be combined in any order to implement the method 1000. Additionally, individual steps may be removed from or added to the method 1000 as needed in the therapy without departing from the spirit and scope of the present disclosure.

At step 1002, the method 1000 includes forming the elongate body 102 having the stylus end 104, the central body 106, the C-shaped handle 108, and the handle end cap 110. Further, the stylus end 104 is connected to the first end 106A of the central body 106 and the second end 106B of the central body 106 is connected to the first end 108A of the of the C-shaped handle 108. Furthermore, the handle end cap 110 is connected to the second end 108B of the C-shaped handle 108. In an aspect, the central body 106, the C-shaped handle 108, the handle end cap 110, and the stylus end 104 are manufactured as individual elements using various known manufacturing process. Further, the first end 106A of the central body 106 is detachably coupled to the stylus end 104 and the second end 106B of the central body 106 is slidably coupled to the first end 108A of the C-shaped handle 108 using the first sliding mechanism 202. The second end 108B of the C-shaped handle 108 is slidably attached to the handle end cap 110 using the second sliding mechanism 204. As such, the central body 106, the stylus end 104, the C-shaped handle 108, and the handle end cap 110 are detachably coupled to form the elongate body 102 of the smart stylus 100.

At step 1004, the method 1000 includes installing the rechargeable battery 602 within the handle end cap 110, into the smart stylus 100. In one aspect, a receiving portion may be defined in the handle end cap 110 to insert the rechargeable battery 602. As such, after forming the elongate body 102, a user may manually place the rechargeable battery 602 within the handle end cap 110 and may remove or replace the rechargeable battery 602 as needed. In another aspect, the rechargeable battery 602 may be installed in the handle end cap 110 during the manufacturing of the smart stylus 100 such that the rechargeable battery 602 become an integral component of the smart stylus 100 and may not be replaceable or removable by the user during the life time of the smart stylus 100.

At step 1006, the method 1000 includes inserting the microcontroller 612 within the central body 106 of the smart stylus 100, as such, the microcontroller 612 receives operating current from the rechargeable battery 602. As explained with reference to the rechargeable battery 602 at the step 1004, the microcontroller 612 may be either installed with the central body 106 during the manufacturing thereof to become an integral portion thereof or the microcontroller 612 may be installed by the user upon forming the elongate body 102 of the smart stylus 100.

At step 1008, the method 1000 includes operatively connecting the microcontroller 612 to the rechargeable battery 602. As such, the rechargeable battery 602 supplies a required power input to the microcontroller 612. At step 1010, the method 1000 includes forming the case 710 to hold the elongate body 102 of the smart stylus 100 and the therapeutic tablet 702. In particular, the case 710 may be formed using an elastomeric thermoplastic, a polymeric plastic, a metal alloy mixed with a plastic, and the like. The case 710 is defined as a rectangular body to accommodate the smart stylus 100 towards a left end of the case 710 and the touch screen 714 towards the right end of the case. The weight receiving slots 718 are defined at the top left corner of the case 710 for the patient to comfortably and conveniently access the plurality of the weights 510.

At step 1012, the method 1000 includes forming the charging port 712 in the case 710. As such, the charging port 712 is configured to mate with the handle end cap 110 of the smart stylus 100. Further, at step 1014, the method 1000 includes installing the electromagnetic coil 604 within the handle end cap 110 and connecting the electromagnetic coil 604 to the rechargeable battery 602. In some aspects, the electromagnetic coil 604 is configured to generate the charging current when the handle end cap 110 is placed adjacent to the charging port 712. The electromagnetic coil 604 is configured to receive the charging current transmitted by the charging port 712 present on the case 710. In some aspects, charging may be wireless charging. At step 1016, the method 1000 includes installing the near field communications unit 614 within the central body 106 and operatively connecting the near field communications unit 614 with the microcontroller 612. The near field communications unit 614 receives instructions from the microcontroller 612 electronically, on a command given by the patient to the microcontroller 612.

At step 1018, the method 1000 includes linking the therapeutic tablet 702 including the touch screen 714 to the microcontroller 612. Furthermore, the therapeutic tablet 702 includes the memory 716, including program instruction including the hand therapy treatment plan and the one or more processors for executing the program instructions to receive near field communications from the near field communications unit 614. Moreover, the therapeutic tablet 702 displays the hand therapy treatment plan and hand therapy exercises upon the touch screen 714. The hand therapy exercises are configured to direct the patient to write upon the touch screen 714 with the stylus end 104 while gripping the C-shaped handle 108, and also, while gripping the first and the second flexible grips 402, 404. The hand therapy treatment plan is embedded into the program instruction stored in the memory 716 of the therapeutic tablet 702. The program instructions are executed by the processor when the patient prompts the system 700 for the hand therapy exercises. When executed, the patient performs the said hand therapy exercises by gripping the smart stylus 100, on the touch screen 714 of the therapeutic tablet 702.

The method 1000 further includes connecting the pressure sensor 610 to the stylus end 104 and connecting the pressure sensor 610 to the microcontroller 612. In addition, the method 1000 includes generating, by the pressure sensor 610, electrical signals in response to an amount of pressure sensed by the pressure sensor 610 when the stylus end 104 contacts the touch screen 714. In other words, when the patient uses the smart stylus 100 on the touch screen 714 of the therapeutic tablet 702, the pressure exerted by the patient on the stylus end 104 is sensed by the pressure sensor 610 and is subsequently relayed on to the microcontroller 612. Furthermore, the method 1000 includes transmitting, by the near field communications unit 614, the electrical signals related to the amount of pressure by near field communication to the therapeutic tablet 702. In some aspects, the method 1000 includes displaying, on the touch screen 714, the hand therapy exercises including grip strength exercises, hand-eye coordination exercises, and interactive games configured to improve motor skills, coordination, and cognitive functions of the patient.

The method 1000 further includes monitoring the progress of the patient by the patient assessment unit 902 located within the therapeutic tablet 702, and comparing, by the patient assessment unit 902, the progress of the patient against the baseline assessment. As described above, the baseline assessment is conducted before the enrollment of the patient in the hand therapy and further assessments are made using the patient assessment unit 902, as the patient progresses in the hand therapy treatment plan. Furthermore, the method 1000 includes generating, by the patient assessment unit 902, the progress report and transmitting, by a wireless communication unit 904 located within the therapeutic tablet 702, the progress report to the remote medical system 906 configured to monitor the progress of the patient.

The first embodiment of the present disclosure is illustrated with respect to FIG. 1 through FIG. 6C. The first embodiment describes the smart stylus 100 for use in hand therapy, including an elongate body 102 having the stylus end 104, the central body 106, the C-shaped handle 108, and the handle end cap 110, wherein the stylus end 104 is connected to the first end 106A of the central body 106, the second end 106B of the central body 106 is connected to the first end 108A of the C-shaped handle 108, wherein the central body 106 is configured to taper in width and depth from the second end 106B of the central body 106 to the first end 106A of the central body 106, wherein the handle end cap 110 is connected to the second end 108B of the C-shaped handle 108. The first sliding mechanism 202 is located between the central body 106 and the first end 108A of the C-shaped handle 108, and the second sliding mechanism 204 is located between the second end 108B of the C-shaped handle 108 and the handle end cap 110, wherein the length of the elongate body 102 depends on an adjustment of the first sliding mechanism 202 and the second sliding mechanism 204.

In an aspect of the smart stylus 100, the outer region 302 of the C-shaped handle 108 includes the first groove 304 which extends from the first end 108A of the C-shaped handle 108 to the second end 108B of the C-shaped handle 108, wherein the first groove 304 has the width in a range of 80% to 90% of the width of the C-shaped handle 108 and the depth in the range of 0.25 to 1.0 cm.

In an aspect of the smart stylus 100, the outer region 306 of the central body 106 from the first end 106A of the central body 106 to about halfway between the first end 106A of the central body 106 and the second end 106B of the central body 106 includes the second groove 308 which matches the first groove 304 of the C-shaped handle 108 in depth and width.

In an aspect, the smart stylus 100 further including the first flexible grip 402 located on the central body 106 halfway between the first end 106A of the central body 106 and the second end 106B of the central body 106, wherein the first flexible grip 402 includes raised lines 402A extending across the central body 106 perpendicular to the central axis 'C1' of the central body 106, and the second flexible grip 404 located on the handle end cap 110, wherein the second flexible grip 404 includes raised lines 404A extending across the handle end cap 110 perpendicular to the central axis 'C2' of the handle end cap 110.

In an aspect, the smart stylus 100 further including the at least two upper weight receiving compartments 502, wherein each upper weight receiving compartment is located on either side of the C-shaped handle 108 near the first end 108A, and the at least two lower weight receiving compartments 504, wherein each lower weight receiving compartment is located on either side of the C-shaped handle 108 near the second end 108B, and the plurality of weights 510, wherein each weight is sized to fit within a respective weight receiving compartment.

In an aspect of the smart stylus 100, the plurality of weights 510 includes the oblong weight 510A and the cylindrical weight 510B, wherein each side of the C-shaped handle 108 includes a weight receiving compartment sized to receive the oblong weight 510A and a weight receiving compartment sized to receive the cylindrical weight 510B.

In an aspect of the smart stylus 100, the elongate body 102 and the C-shaped handle 108 are made of the elastomeric thermoplastic.

In an aspect, the smart stylus 100 further including the rechargeable battery 602 located within the handle end cap 110.

In an aspect, the smart stylus 100 further including the pressure sensor 610 located within the elongate body 102 and connected to the stylus end 104.

In an aspect, the smart stylus 100 further including the microcontroller 612 located within the central body 106, wherein the microcontroller 612 is operatively connected to the rechargeable battery 602 and the pressure sensor 610, and the near field communications unit 614 located within the central body 106 and operatively connected with the microcontroller 612.

The second embodiment of the present disclosure is illustrated with respect to FIG. 7A through FIG. 9. The second embodiment describes the smart stylus therapeutic system 700 for use in hand therapy, including an elongate body 102 having the stylus end 104, the central body 106, the C-shaped handle 108, and the handle end cap 110, wherein the stylus end 104 is connected to the first end 106A of the central body 106, the second end 106B of the central body 106 is connected to the first end 108A of the C-shaped handle 108, and the handle end cap 110 is connected to the second end 108B of the C-shaped handle 108, the rechargeable battery 602 located within the handle end cap 110, the microcontroller 612 located within the central body 106, wherein the microcontroller 612 is operatively connected to the rechargeable battery 602, the near field communications unit 614 located within the central body 106 and operatively connected with the microcontroller 612, the therapeutic tablet 702 including the touch screen 714, wherein the therapeutic tablet 702 includes the memory 716 including program instructions including the hand therapy treatment plan and the one or more processors configured to execute the program instructions to receive near field communications from the near field communications unit 614 and display the hand therapy treatment plan and the hand therapy exercises upon the touch screen 714, wherein the hand therapy exercises are configured to direct the patient to write upon the touch screen 714 with the stylus end 104 while gripping the C-shaped handle 108, the case 710 configured to hold the elongate body 102 and the therapeutic tablet 702, the charging port 712 located on the case 710, wherein the charging port 712 is configured to mate with the handle end cap 110, the rechargeable battery located with the central body 106, the electromagnetic coil 604 located within the handle end cap 110 and connected to the rechargeable battery 602, wherein the electromagnetic coil 604 is configured to generate the charging current when the handle end cap 110 is placed adjacent to the charging port 712.

In an aspect of the smart stylus therapeutic system 700, the therapeutic tablet 702 is configured to receive the battery charge status by near field communications from the microcontroller 612 and display the battery charge status on the touch screen 714.

In an aspect, the smart stylus therapeutic system 700 further including the pressure sensor 610 located within the elongate body 102 and connected to the stylus end 104, wherein the pressure sensor 610 is connected to the microcontroller 612, wherein the pressure sensor 610 is configured to generate electrical signals in response to an amount of pressure sensed by the pressure sensor 610 when the stylus end 104 contacts the touch screen 714, and wherein the microcontroller 612 is configured to transmit the electrical signals related to the amount of pressure by near field communications to the therapeutic tablet 702.

In an aspect, the smart stylus therapeutic system 700 further including the at least two upper weight receiving compartments 502, wherein each upper weight receiving compartment is located on either side of the C-shaped handle 108 near the first end 108A, and the at least two lower weight receiving compartments 504, wherein each lower weight receiving compartment is located on either side of the C-shaped handle 108 near the second end 108B, and the plurality of weights 510, wherein each weight is sized to fit within the respective weight receiving compartment, wherein the plurality of weights are stored in the weight receiving slots 718 in the case 710, and wherein the therapeutic tablet 702 is configured to receive the electrical signals related to the amount of pressure of the stylus end 104 against the touch screen 714 and select the weight from the plurality of weights 510 in accordance with the hand therapy treatment plan.

In an aspect of the smart stylus therapeutic system 700, the hand therapy exercises include grip strength exercises, hand-eye coordination exercises, and interactive games configured to improve motor skills, coordination, and cognitive functions.

In an aspect, the smart stylus therapeutic system 700 further including the patient assessment unit 902 located within the therapeutic tablet 702, wherein the patient assessment unit 902 is configured to monitor the progress of the patient against the baseline assessment and generate the progress report, and the wireless communication unit 904 located within the therapeutic tablet 702, wherein the wireless communication unit 904 is configured to wirelessly transmit the progress report to the remote medical system 906 configured to monitor the progress of the patient.

The third embodiment of the present disclosure is illustrated with respect to FIG. 10. The third embodiment describes the method 1000 of using the smart stylus 100 in the hand therapy, including forming the elongate body 102 having the stylus end 104, the central body 106, the C-shaped handle 108, and the handle end cap 110, wherein the stylus end 104 is connected to the first end 106A of the central body 106, the second end 106B of the central body 106 is connected to the first end 108A of the C-shaped handle 108, and the handle end cap 110 is connected to the second end 108B of the C-shaped handle 108, installing the rechargeable battery 602 within the handle end cap 110, inserting the microcontroller 612 within the central body 106, operatively connecting the microcontroller 612 to the rechargeable battery 602, forming the case 710 configured to hold the elongate body 102 and the therapeutic tablet 702, forming the charging port 712 in the case 710, wherein the charging port 712 is configured to mate with the handle end cap 110, installing the electromagnetic coil 604 within the handle end cap 110 and connecting the electromagnetic coil 604 to the rechargeable battery 602, wherein the electromagnetic coil 604 is configured to generate the charging current when the handle end cap 110 is placed adjacent to the charging port 712, installing the near field communications unit 614 within the central body 106 and operatively connecting the near field communications unit 614 with the microcontroller 612, and linking the therapeutic tablet 702 including the touch screen 714 to the microcontroller 612, wherein the therapeutic tablet 702 includes the memory 716 including program instructions including the hand therapy treatment plan and the one or more processors configured to execute the program instructions to receive near field communications from the near field communications unit 614 and display the hand therapy treatment plan and the hand therapy exercises upon the touch screen 714, wherein the hand therapy exercises are configured to direct the patient to write upon the touch screen 714 with the stylus end 104 while gripping the C-shaped handle 108.

In an aspect, the method 1000 further including connecting the pressure sensor 610 to the stylus end 104 and connecting the pressure sensor 610 to the microcontroller 612, generating, by the pressure sensor 610, electrical signals in response to the amount of pressure sensed by the pressure sensor 610 when the stylus end 104 contacts the touch screen 714, and transmitting, by the near field communications unit 614, the electrical signals related to the amount of pressure by near field communication to the therapeutic tablet 702.

In an aspect, the method 1000 further including displaying, on the touch screen 714, the hand therapy exercises including grip strength exercises, hand-eye coordination exercises, and interactive games configured to improve motor skills, coordination, and cognitive functions of the patient.

In an aspect, the method 1000 further including monitoring the progress of the patient by the patient assessment unit 902 located within the therapeutic tablet 702, comparing, by the patient assessment unit 902, the progress of the patient against the baseline assessment, generating, by the patient assessment unit 902, the progress report, and transmitting, by the wireless communication unit 904 located within the therapeutic tablet 702, the progress report to the remote medical system 906 configured to monitor the progress of the patient.

Figure 11:
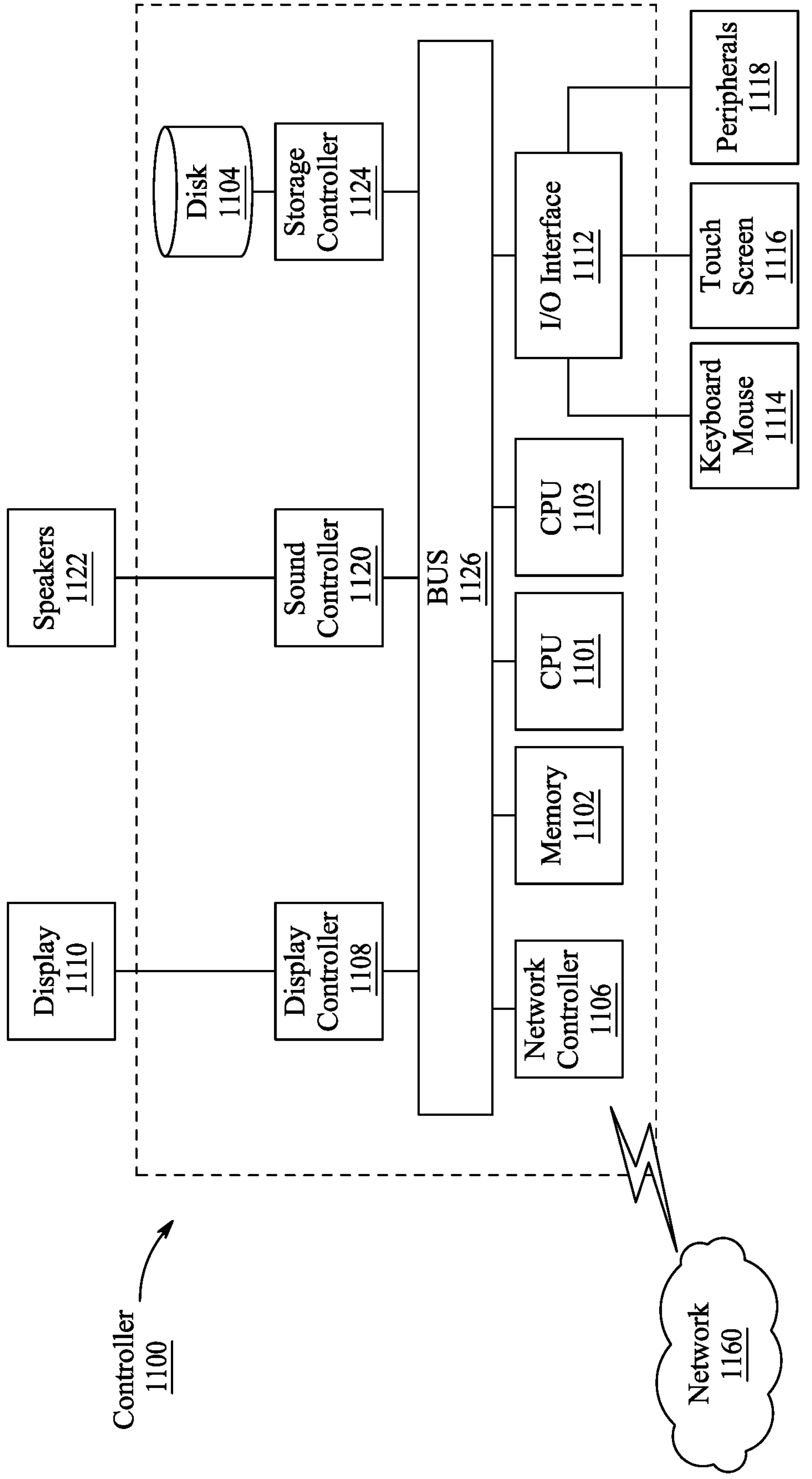
FIG. 11 is an illustration of a non-limiting example of details of computing hardware used in a computing system, according to certain embodiments.

Next, further details of the hardware description of the computing environment according to exemplary aspects is described with reference to FIG. 11. In FIG. 11, a controller 1100 is described, representative of the system 700 of FIG. 7A in which the controller is a computing device which includes a CPU 1101 which performs the processes described above/below. The process data and instructions may be stored in memory 1102. These processes and instructions may also be stored on a storage medium disk 1104 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 1101, 1103 and an operating system such as Microsoft Windows 7, Microsoft Windows 10, Microsoft Windows 11, UNIX, Solaris, LINUX, Apple MAC-OS and other systems known to those skilled in the art.

The hardware elements in order to achieve the computing device may be realized by various circuitry elements, known to those skilled in the art. For example, CPU 1101 or CPU 1103 may be a Xenon or Core processor from Intel of America or an Opteron processor from AMD of America, or may be other processor types that would be recognized by one of ordinary skill in the art. Alternatively, the CPU 1101, 1103 may be implemented on an FPGA, ASIC, PLD or using discrete logic circuits, as one of ordinary skill in the art would recognize. Further, CPU 1101, 1103 may be implemented as multiple processors cooperatively working in parallel to perform the instructions of the inventive processes described above.

The computing device in FIG. 11 also includes a network controller 1106, such as an Intel Ethernet PRO network interface card from Intel Corporation of America, for interfacing with network 1160. As can be appreciated, the network 1160 can be a public network, such as the Internet, or a private network such as an LAN or WAN network, or any combination thereof and can also include PSTN or ISDN sub-networks. The network 1160 can also be wired, such as an Ethernet network, or can be wireless such as a cellular network including EDGE, 3G, 4G and 5G wireless cellular systems. The wireless network can also be Wi-Fi, Bluetooth, or any other wireless form of communication that is known.

The computing device further includes a display controller 1108, such as a NVIDIA GeForce GTX or Quadro graphics adaptor from NVIDIA Corporation of America for interfacing with display 1110, such as a Hewlett Packard HPL2445w LCD monitor. A general purpose I/O interface 1112 interfaces with a keyboard and/or mouse 1114 as well as a touch screen panel 1116 on or separate from display 1110. General purpose I/O interface also connects to a variety of peripherals 1118 including printers and scanners, such as an Office-Jet or Desk-Jet from Hewlett Packard.

A sound controller 1120 is also provided in the computing device such as Sound Blaster X-Fi Titanium from Creative, to interface with speakers/microphone 1122 thereby providing sounds and/or music.

The general purpose storage controller 1124 connects the storage medium disk 1104 with communication bus 1126, which may be an ISA, EISA, VESA, PCI, or similar, for interconnecting all of the components of the computing device. A description of the general features and functionality of the display 1110, keyboard and/or mouse 1114, as well as the display controller 1108, storage controller 1124, network controller 1106, sound controller 1120, and general purpose I/O interface 1112 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 12.

Figure 12:
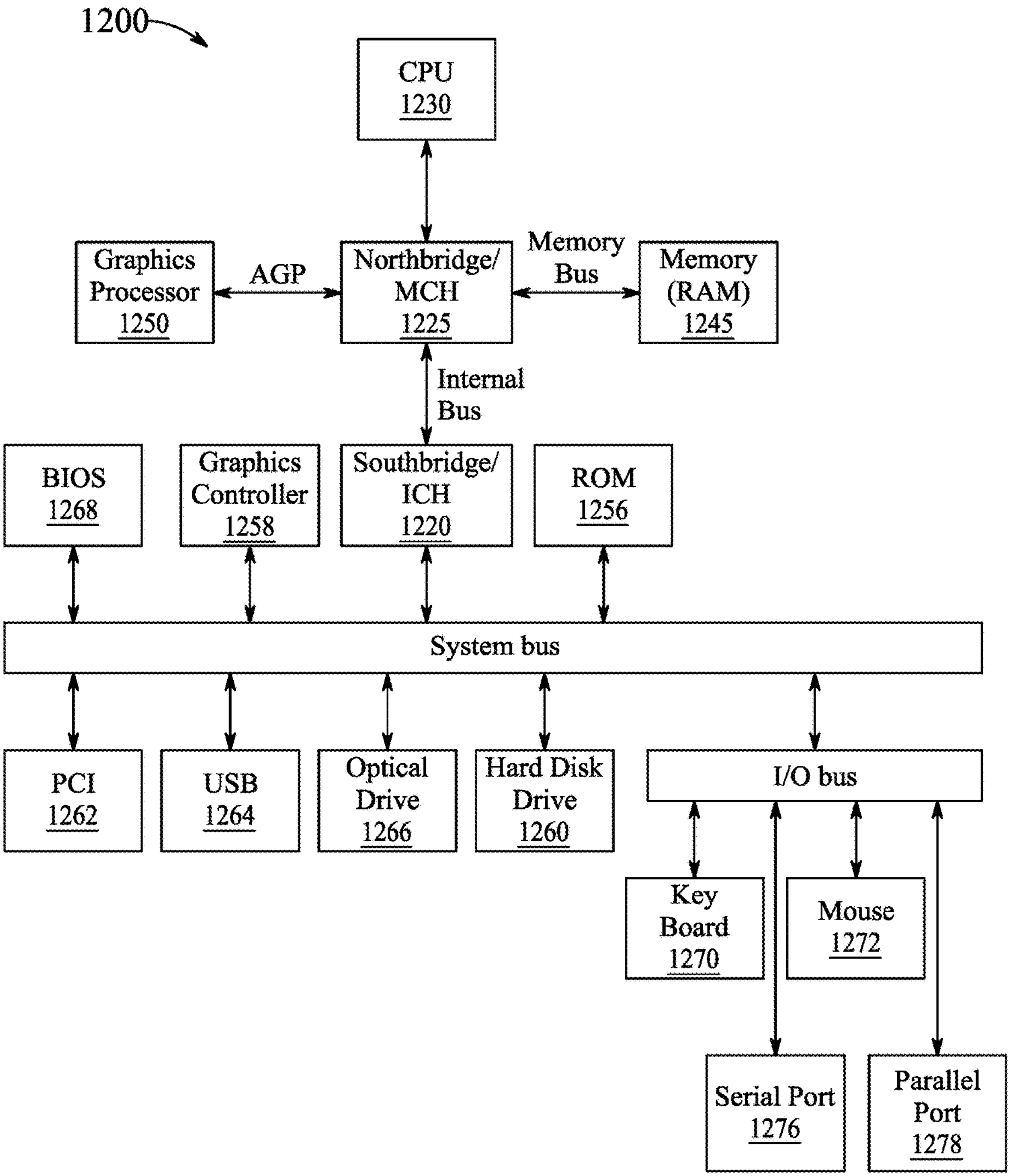
FIG. 12 is an exemplary schematic diagram of a data processing system used within the computing system, according to certain embodiments.

FIG. 12 shows a schematic diagram of a data processing system, according to certain aspects, for performing the functions of the exemplary aspects. The data processing system is an example of a computer in which code or instructions implementing the processes of the illustrative aspects may be located.

In FIG. 12, data processing system 1200 employs a hub architecture including a north bridge and memory controller hub (NB/MCH) 1225 and a south bridge and input/output (I/O) controller hub (SB/ICH) 1220. The central processing unit (CPU) 1230 is connected to NB/MCH 1225. The NB/MCH 1225 also connects to the memory 1245 via a memory bus and connects to the graphics processor 1250 via an accelerated graphics port (AGP). The NB/MCH 1225 also connects to the SB/ICH 1220 via an internal bus (e.g., a unified media interface or a direct media interface). The CPU Processing unit 1230 may contain one or more processors and even may be implemented using one or more heterogeneous processor systems.

Figure 13:
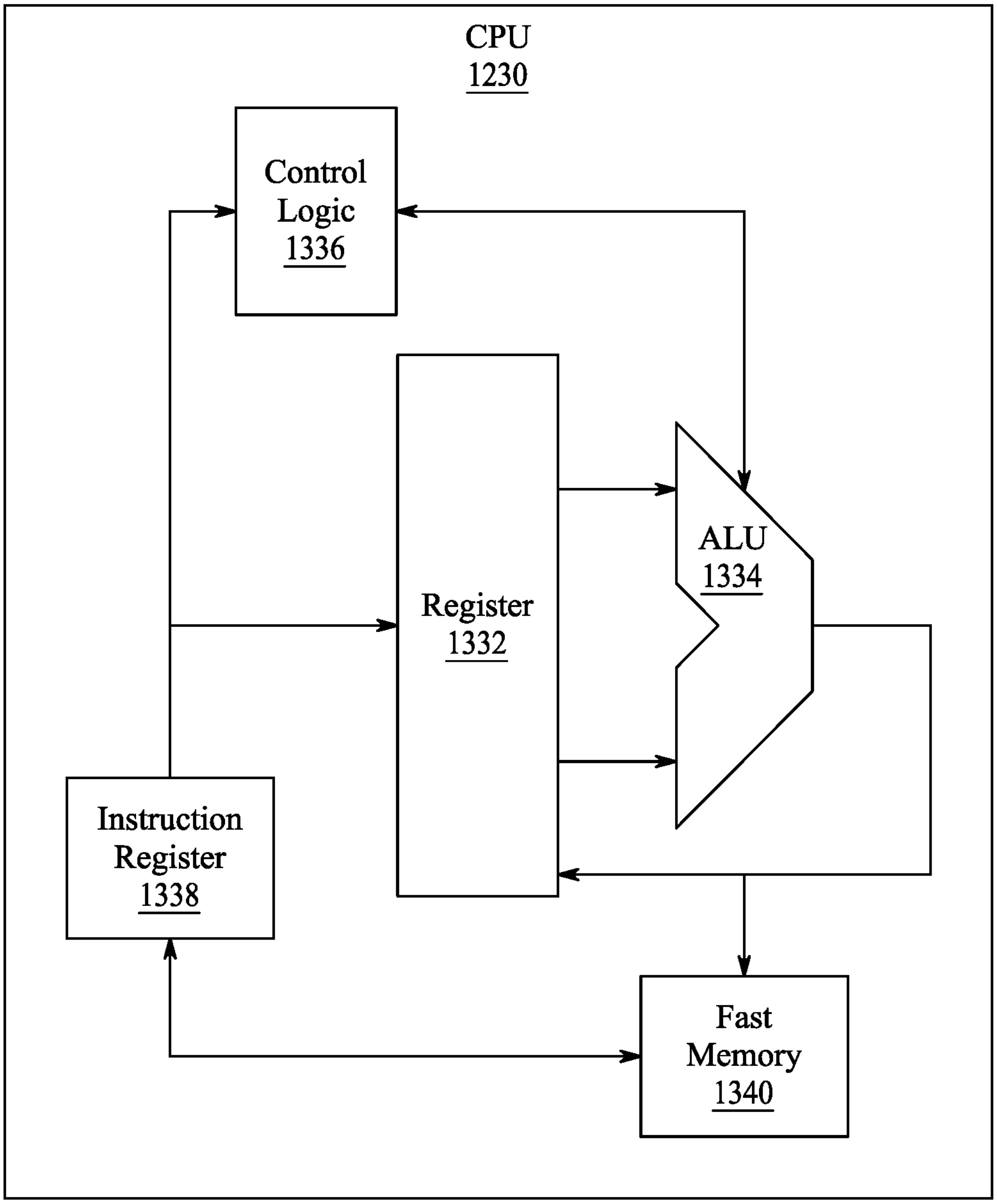
FIG. 13 is an exemplary schematic diagram of a processor used with the computing system, according to certain embodiments.

For example, FIG. 13 shows one implementation of CPU 1230. In one implementation, the instruction register 1338 retrieves instructions from the fast memory 1340. At least part of these instructions are fetched from the instruction register 1338 by the control logic 1336 and interpreted according to the instruction set architecture of the CPU 1230. Part of the instructions can also be directed to the register 1332. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 1334 that loads values from the register 1332 and performs logical and mathematical operations on the loaded values according to the instructions. The results from these operations can be feedback into the register and/or stored in the fast memory 1340. According to certain implementations, the instruction set architecture of the CPU 1230 can use a reduced instruction set architecture, a complex instruction set architecture, a vector processor architecture, a very large instruction word architecture. Furthermore, the CPU 1230 can be based on the Von Neuman model or the Harvard model. The CPU 1230 can be a digital signal processor, an FPGA, an ASIC, a PLA, a PLD, or a CPLD. Further, the CPU 1230 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 12, the data processing system 1200 can include that the SB/ICH 1220 is coupled through a system bus to an I/O Bus, a read only memory (ROM) 1256, universal serial bus (USB) port 1264, a flash binary input/output system (BIOS) 1268, and a graphics controller 1258. PCI/PCIe devices can also be coupled to SB/ICH 1288 through a PCI bus 1262.

The PCI devices may include, for example, Ethernet adapters, add-in cards, and PC cards for notebook computers. The Hard disk drive 1260 and CD-ROM 1266 can use, for example, an integrated drive electronics (IDE) or serial advanced technology attachment (SATA) interface. In one implementation the I/O bus can include a super I/O (SIO) device.

Further, the hard disk drive (HDD) 1260 and optical drive 1266 can also be coupled to the SB/ICH 1220 through a system bus. In one implementation, a keyboard 1270, a mouse 1272, a parallel port 1278, and a serial port 1276 can be connected to the system bus through the I/O bus. Other peripherals and devices that can be connected to the SB/ICH 1220 using a mass storage controller such as SATA or PATA, an Ethernet port, an ISA bus, a LPC bridge, SM-bus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Figure 14:
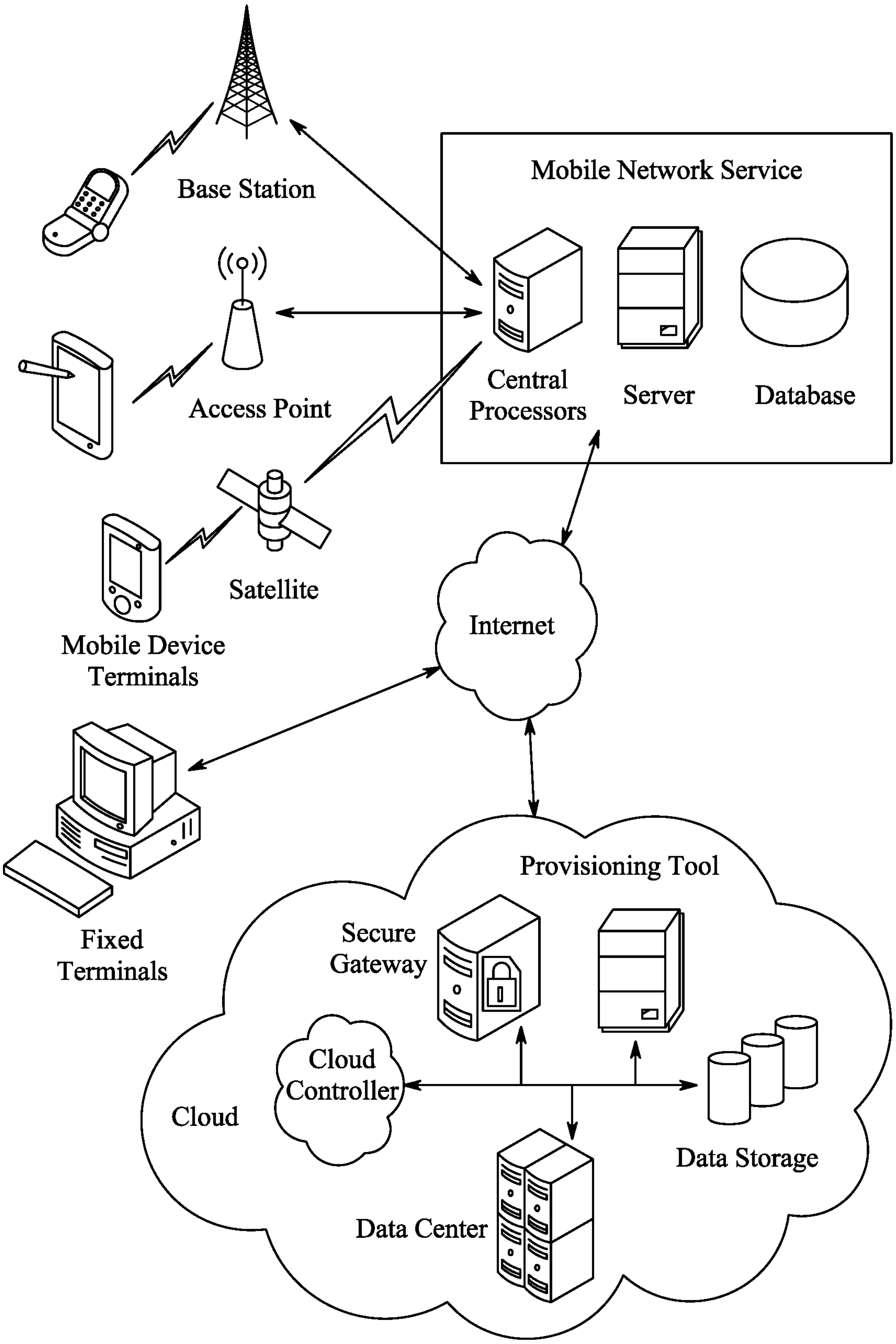
FIG. 14 is an illustration of a non-limiting example of distributed components which may share processing with a controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 14, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

According to the present disclosure, the smart stylus 100, the smart stylus therapeutic system 700, and the method 1000 provide an efficient, adaptive, and dynamic way of treating paralysis and loss of motor skills caused by stroke, or any other similar illness. The smart stylus 100, the smart stylus therapeutic system 700, and the method 1000 are designed for ease of operation and adaptation in a plurality of environments. As such, the smart stylus 100 and the smart stylus therapeutic system 700 provide advanced prospects of adaptation in a plurality of medical rehabilitation centers, physiological rehabilitation centers, and neurological rehabilitation centers. Furthermore, the smart stylus 100 provides a gamified experience to the patient in order to enhance rehabilitation therapy time of the patient. The system 700 may provide visual cues, prompts, and engaging activities that may motivate the patient during a particular, tailored therapy session. Therefore, the system 700 may result in better overall patient rehabilitation. The smart stylus therapeutic system 700 may eliminate the stigma associated with stroke rehabilitation therapy as previously recorded in a younger generation of stroke patients. In some aspects, the smart stylus therapeutic system 700 may be capable of receiving over the air (OTA) updates for remote upgradation of the system 700.

Numerous modifications and variations of the present disclosure are possible in light of the above teachings. It is therefore to be understood that within the scope of the appended claims, the invention may be practiced otherwise than as specifically described herein.

The invention claimed is:

1. A smart stylus therapeutic system for use in hand therapy, comprising:

an elongate body having a stylus end, a central body, a C-shaped handle, and a handle end cap, wherein the stylus end is connected to a first end of the central body, a second end of the central body is connected to a first end of the C-shaped handle, and the handle end cap is connected to a second end of the C-shaped handle;

a rechargeable battery located within the handle end cap;

a microcontroller located within the central body, wherein the microcontroller is operatively connected to the rechargeable battery;

a near field communications unit located within the central body and operatively connected with the microcontroller;

a therapeutic tablet including a touch screen, wherein the therapeutic tablet includes a memory including program instructions including a hand therapy treatment plan and one or more processors configured to execute the program instructions to receive near field communications from the near field communications unit and display the hand therapy treatment plan and hand therapy exercises upon the touch screen, wherein the hand therapy exercises are configured to direct a patient to write upon the touch screen with the stylus end while gripping the C-shaped handle;

a case configured to hold the elongate body and the therapeutic tablet;

a charging port located on the case, wherein the charging port is configured to mate with the handle end cap, wherein the rechargeable is battery located with the central body; and an electromagnetic coil located within the handle end cap and connected to the rechargeable battery, wherein the electromagnetic coil is configured to generate a charging current when the handle end cap is placed adjacent to the charging port.

2. The smart stylus therapeutic system of claim 1, wherein the therapeutic tablet is configured to receive a battery charge status by near field communications from the microcontroller and display the battery charge status on the touch screen.

3. The smart stylus therapeutic system of claim 1, further comprising:

a pressure sensor located within the elongate body and connected to the stylus end, wherein the pressure sensor is connected to the microcontroller, wherein the pressure sensor is configured generate electrical signals in response to an amount of pressure sensed by the pressure sensor when the stylus end contacts the touch screen, and wherein the microcontroller is configured to transmit the electrical signals related to the amount of pressure by near field communications to the therapeutic tablet.

4. The smart stylus therapeutic system of claim 3, further comprising:

at least two upper weight receiving compartments, wherein each upper weight receiving compartment is located on either side of the C-shaped handle near the first end; and at least two lower weight receiving compartments, wherein each lower weight receiving compartment is located on either side of the C-shaped handle near the second end; and a plurality of weights, wherein each weight is sized to fit within a respective weight receiving compartment, wherein the plurality of weights is stored in weight receiving slots in the case, and wherein the therapeutic tablet is configured to receive the electrical signals related to the amount of pressure of the stylus end against the touch screen and select a weight from the plurality of weights in accordance with the hand therapy treatment plan.

5. The smart stylus therapeutic system of claim 1, wherein the hand therapy exercises include grip strength exercises, hand-eye coordination exercises, and interactive games configured to improve motor skills, coordination, and cognitive functions.

6. The smart stylus therapeutic system of claim 5, further comprising:

a patient assessment unit located within the therapeutic tablet, wherein the patient assessment unit is configured to monitor a progress of the patient against a baseline assessment and generate a progress report; and a wireless communication unit located within the therapeutic tablet, wherein the wireless communication unit is configured to wirelessly transmit the progress report to a remote medical system configured to monitor the progress of the patient.

7. A method of using a smart stylus in hand therapy, comprising:

forming an elongate body having a stylus end, a central body, a C-shaped handle, and a handle end cap, wherein the stylus end is connected to a first end of the central body, a second end of the central body is connected to a first end of the C-shaped handle, and the handle end cap is connected to a second end of the C-shaped handle;

installing a rechargeable battery within the handle end cap;

inserting a microcontroller within the central body;

operatively connecting the microcontroller to the rechargeable battery;

forming a case to hold the elongate body and the therapeutic tablet;

forming a charging port in the case, wherein the charging port is configured to mate with the handle end cap;

installing an electromagnetic coil within the handle end cap and connecting the electromagnetic coil to the rechargeable battery, wherein the electromagnetic coil is configured to generate a charging current when the handle end cap is placed adjacent to the charging port;

installing a near field communications unit within the central body and operatively connecting the near field communications unit with the microcontroller; and linking the therapeutic tablet including a touch screen to the microcontroller, wherein the therapeutic tablet includes a memory including program instructions including a hand therapy treatment plan and one or more processors configured to execute the program instructions to receive near field communications from the near field communications unit and display the hand therapy treatment plan and hand therapy exercises upon the touch screen, wherein the hand therapy exercises are configured to direct a patient to write upon the touch screen with the stylus end while gripping the C-shaped handle.

8. The method of claim 7, further comprising:

connecting a pressure sensor to the stylus end and connecting the pressure sensor to the microcontroller;

generating, by the pressure sensor, electrical signals in response to an amount of pressure sensed by the pressure sensor when the stylus end contacts the touch screen, and transmitting, by the near field communications unit, the electrical signals related to the amount of pressure by near field communication to the therapeutic tablet.

9. The method of claim 8, further comprising:

displaying, on the touch screen, the hand therapy exercises including grip strength exercises, hand-eye coordination exercises, and interactive games configured to improve motor skills, coordination, and cognitive functions of the patient.

10. The method of claim 9, further comprising:

monitoring a progress of the patient by a patient assessment unit located within the therapeutic tablet;

comparing, by the patient assessment unit, the progress of the patient against a baseline assessment;

generating, by the patient assessment unit, a progress report; and transmitting, by a wireless communication unit located within the therapeutic tablet, the progress report to a remote medical system configured to monitor the progress of the patient.

* * * * *